(12) United States Patent
Smrcka et al.

(10) Patent No.: US 8,748,480 B2
(45) Date of Patent: Jun. 10, 2014

(54) METHODS FOR TREATING OPIOID TOLERANCE

(71) Applicant: University of Rochester, Rochester, NY (US)

(72) Inventors: Alan V. Smrcka, Rochester, NY (US); Jose Font, Fairport, NY (US); Tabetha Bonacci, Kimball, MN (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 13/630,995

(22) Filed: Sep. 28, 2012

(65) Prior Publication Data

US 2013/0116313 A1 May 9, 2013

Related U.S. Application Data

(63) Continuation of application No. 11/885,981, filed as application No. PCT/US2006/008031 on Mar. 7, 2006, now abandoned.

(60) Provisional application No. 60/659,267, filed on Mar. 7, 2005.

(51) Int. Cl.
*A61K 31/352* (2006.01)
*G01N 33/68* (2006.01)

(52) U.S. Cl.
USPC .............................................. 514/454; 435/4

(58) Field of Classification Search
None
See application file for complete search history.

(56) References Cited

U.S. PATENT DOCUMENTS

| | | | |
|---|---|---|---|
| 6,168,927 B1 | 1/2001 | King et al. | |
| 7,097,993 B2 | 8/2006 | Anderson et al. | |
| 2002/0106690 A1 | 8/2002 | Leberer et al. | |
| 2003/0235863 A1 | 12/2003 | Sklar et al. | |
| 2004/0121330 A1 | 6/2004 | Feder et al. | |
| 2004/0253668 A1 | 12/2004 | Ramanathan et al. | |

FOREIGN PATENT DOCUMENTS

WO 00/45179 8/2000

OTHER PUBLICATIONS

Bonacci et al., "Differential Targeting of Gβγ-Submit Signaling with Small Molecules," 2006, *Science* 312:443-446.
Davis et al., "Structural and Molecular Characterization of a Preferred Protein Interaction Surface on G Protein βγ Subunits," 2005, *Biochemistry* 44:10593-10604.
Ford et al., "Molecular basis for interactions of G protein beta gamma subunits with effectors," 1998, *Science* 280:1271-1274.
Ford, et al., "Molecular basis for Interactions of G Protein beta gamma Subunits with Effectors—Supplementary Information to Figure 3," vol. 280, 1998, XP002598224, Science Magazine, retrieved from internet: http://www.sciencemag.org/feature/data/974104.dt [retrieved Oct. 2, 2012.
Gao et al., "G protein beta subunit [*Homo sapiens*]," GenBank: AAA35922.1, published Jun. 11, 1993.
Gaudet et al., "Crystal structure at 2.4 angstroms resolution of the complex of transducin beta gamma and its regulator, phosducin," 1996, *Cell* 87:577-588.
Ghosh et al., "Receptor- and nucleotide Exchange-independent Mechanisms for Promoting G Protein Subunit Dissociation," 2003, *J Biol Chem.* 278(37):34747-50.
Goubaeva et al., "Stimulation of Cellular Signaling and G Protein Subunit Dissociation by G Protein beta gamma Subunit-binding Peptides," 2003, *J Biol Chem* 278(22):13634-19641.
Lambright et al., "The 2.0 angstroms crystal structure of a heterotrimeric G protein," 1996, *Nature* 379:311-319.
Li et al., "Sites for Galpha Binding on the G Protein Beta Subunit Overlap with Sites for Regulation of Phospholipase Cbeta and Adenylyl Cyclase," 1998, *J Biol Chem* 273(26):16265-16272.
Lodowski et al., "Keeping G Proteins at Bay: A Complex Between G Protein-Coupled Receptor Kinase 2 and G beta gamma," 2003, *Science* 300:1256-1262.
Loew et al., "Phosducin induces a structural change in transducing beta gamma," 1998, *Structure* 6(8):1007-1019.
Novac et al., "Inhibitors of protein synthesis identified by a high throughput multiplexed translation screen," *Nucleic Acids Research*, 2004, 32(3):902-915.
Ray et al., "G-protein beta-subunit [*Rattus norvegicus*]," GenBank: AAA62620.1, published Mar. 3, 1995.
Sarvazyan et al., "Determinants of gilalpha and beta gamma binding. Measuring high affinity interactions in a lipid environment using flow cytometry," 1998, *J Biol Chem* 273(14):7934-7940.
Scott et al., "Evidence that a protein-protein interaction 'hot spot' on heterotrimeric G protein beta gamma subunits is used for recognition of a subclass of effectors," 2001, *EMBO J.* 20(4):767-776.
Snow et al., "Fidelity of G protein beta-subunit association by the G protein gamma-subunit-like domains of RGS6, RGS7 and RGS11," 1999, *Proc Natl Acad Sci USA* 96:6489-6494.
Sondek et al., "Crystal structure of a G-protein beta gamma dimer at 2.1A resolution," 1996, *Nature* 379:369-374.
Wall et al., "The structure of the G protein heterotrimer Gi alpha 1 beta 1 gamma 2," 1995, *Cell* 83:1047-1058.
Yao, et al. "Addicting drugs utilize a synergistic molecular mechanism in common requiring adenosine and Gi-beta gamma dimers," 2003, *PNAS* 100(24):14379-14384.
Zhou, et al., "Selective regulation of N-type Ca channels by different combinations of G-protein beta/gamma subunits and RGS proteins,": 2000, *J Neurosci* 20(19):7143-7148.
European Search Opinion for EP Application No. 08827151.5, based on PCT/US08/61757, dated Aug. 6, 2010.
Annex to Communication from EPO Examining Division, for EP Application No. 08827151.5, based on PCT/US08/61757, dated Jun. 4, 2011.
Written Opinion of the International Search Authority for International Application No. PCT/US06/08031, dated Jun. 25, 2007.
International Search Report for International Application No. PCT/US06/08031, dated Jul. 2, 2007.
Supplementary European Search Report for EP Application No. 06748307.3, dated Aug. 26, 2010.

(Continued)

*Primary Examiner* — Ruixiang Li
(74) *Attorney, Agent, or Firm* — Riverside Law LLP

(57) ABSTRACT

The present invention relates to methods for identifying agents which bind to specific amino acid residues of the protein interaction site of G protein β protein subunit. Compounds identified in accordance with the assay of the invention and methods for using the compound for modulating at least one activity of a G protein are also provided.

5 Claims, 2 Drawing Sheets

(56) References Cited

OTHER PUBLICATIONS

First Office Action for Japanese Patent Application No. 2008-500834, "Compositions and Methods for Inhibiting G Protein Signaling", issued Oct. 24, 2011.

First Office Action for Chinese Patent Application No. 200680015546.8, "Compositions and Methods for Inhibiting G Protein Signaling," issued Sep. 17, 2010.

Second Office Action for Chinese Patent Application No. 200680015546.8, "Compositions and Methods for Inhibiting G Protein Signaling," issued Jul. 26, 2011.

Third Office Action for Chinese Patent Application No. 200680015546.8, "Compositions and Methods for Inhibiting G Protein Signaling," issued May 2, 2012.

Examiner's first report on (Australian) patent application No. 2006220652, "Compositions and Methods for Inhibiting G Protein Signaling," issued Oct. 6, 2010.

Examiner's report No. 2 on (Australian) patent application No. 2006220652, "Compositions and Methods for Inhibiting G Protein Signaling," issued Nov. 21, 2011.

METHODS FOR TREATING OPIOID TOLERANCE

CROSS-REFERENCE TO RELATED APPLICATION

The present application is a continuation of and claims priority to U.S. patent application Ser. No. 11/885,981, filed Oct. 23, 2008, which is 35 U.S.C. §371 national phase application from, and claiming priority to, International Application No. PCT/US2006/008031, filed Mar. 7, 2006, and published under PCT Article 21(2) in English, which claims the benefit of U.S. Provisional Application No. 60/659,267, filed on Mar. 7, 2005, all of which applications are hereby incorporated by reference in their entireties herein.

STATEMENT REGARDING FEDERALLY SPONSORED RESEARCH OR DEVELOPMENT

This invention was made with government support under grant numbers GM60286 and DK46371 awarded by the National Institutes of Health. The U.S. government has certain rights in this invention.

BACKGROUND OF THE INVENTION

Five mammalian isoforms of the G protein β subunit (37 kDa) and twelve isoforms of G protein γ (7.8 kDa) have been identified (Offermanns (2003) *Prog. Biophys. Mol. Biol.* 83:101-30). Obligate heterodimers composed of G protein β and γ subunits (Gβγ) function as regulatory molecules in various pathways in eukaryotic cells (Neves, et al. (2002) *Science* 296:1636-9; Clapham and Neer (1997) *Annu. Rev. Pharmacol. Toxicol.* 37:167-203). First characterized as a guanine nucleotide dissociation inhibitor (GDI), Gβγ associates tightly with GDP-bound G protein α subunits (Gα) and thereby constitutes the basal form of the G protein heterotrimer in which neither Gα nor Gβγ are active in signaling. Agonist-stimulated G protein coupled receptors (GPCRs) catalyze the exchange of GDP for GTP upon Gα and release of Gβγ from the heterotrimer complex, liberating two active signaling species: Gα•GTP and Gβγ. Targets of Gβγ signaling include the G protein-regulated inward-rectifying potassium channel (GIRK) (Krapivinsky, et al. (1993) *J. Biol. Chem.* 273:16946-52); type I, type II, and type IV isoforms of adenylyl cyclase (Tang and Gilman (1991) *Science* 254:1500-3; Sunahara, et al. (1996) *Annu. Rev. Pharmacol. Toxicol.* 36:461-80); mitogen-activated protein kinase (MAPK) (Schwindinger and Robishaw (2001) *Oncogene* 20:1653-60); phosphotidylinositol-3-kinase (PI3K) (Schwindinger and Robishaw (2001) supra); phosducin (Schulz (2001) *Pharmacol Res* 43:1-10); at least two members of the G protein receptor kinase (GRK) family (Koch, et al. (1993) *J. Biol. Chem.* 268:8256-60; Inglese, et al. (1994) *Proc. Natl. Acad. Sci. USA* 91:3637-41); and other plextrinhomology (PH) domain-containing proteins including the dynamins (Lin, et al, (1998) *Proc. Natl. Acad. Sci. USA* 95:5057-60; Scaife and Margolis (1997) *Cell Signal* 9:395-401) and the β1, β2, and β3 isoforms of phospholipase C β (PLC β) (Sternweis and Smrcka (1992) *Trends Biochem. Sci.* 17:502-6; Li, et al. (1998) *J. Biol. Chem.* 273:16265-72) and many others.

Gβ is a cone-shaped toroidal structure composed of seven four-stranded β-sheets arranged radially about a central axis (Wall, et al. (1995) *Cell* 83:1047-58; Lambright, et al. (1996) *Nature* 379:311-9). Each β-sheet is formed from elements of two consecutive WD-40 repeats, named for a conserved C-terminal Trp-Asp sequence in each repeat (Gettemans, et al. (2003) *Sci STKE* 2003:PE27). The Gγ subunit, an extended helical molecule, is nested in a hydrophobic channel that runs across the base of the cone. The slightly narrower, "top" surface of the Gβ cone is the main binding site of Gα (through its switch II region) (Wall, et al. (1995) supra; Lambright, et al. (1996) supra), phosducin (Loew, et al. (1998) *Structure* 6:1007-19; Gaudet, et al. (1996) *Cell* 87:577-88), and GRK2 (Lodowski, et al. (2003) *Science* 300:1256-62), as shown by the crystal structures of these complexes. Mutational analysis indicates that many interaction partners of Gβγ, including PLC β2 and adenylyl cyclase, bind to the same surface (Li, et al. (1998) supra; Ford, et al. (1998) *Science* 280:1271-4). Sites located along the sides of the Gβ torus serve as auxiliary binding surfaces that are specifically recognized by certain Gβγ targets, exemplified in the crystal structures of Gα and phosducin bound to Gβγ (Wall, et al. (1995) supra; Loew, et al. (1998) supra; Gaudet, et al. (1996) supra; Wall, et al. (1998) *Structure* 6:1169-83).

Phage display of randomized peptide libraries has been used to identify sequence requirements for binding and screen for peptide that bind to $Gβ_1γ_2$ dimers (Scott, et al. (2001) *EMBO J.* 20:767-76). Although billions of individual clones were screened, most of the peptides that bound $Gβ_1γ_2$ could be classified into four, unrelated groups based on amino acid sequence. One of these groups included a linear peptide (the "SIRK" peptide) with the sequence Ser-Ile-Arg-Lys-Ala-Leu-Asn-Ile-Leu-Gly-Tyr-Pro-Asp-Tyr-Asp (SEQ ID NO:1). The SIRK peptide inhibited PLC β2 activation by $Gβ_1γ_2$ subunits with an $IC_{50}$ of 5 μM and blocked activation of PI3K. In contrast, the SIRK peptide had little or no effect on $Gβ_1γ_2$ regulation of type I adenylyl cyclase or voltage-gated N-type $Ca^{++}$ channel activity (Scott, et al. (2001) supra). This demonstrated that selective inhibition of Gβγ binding partners could be achieved. Peptides belonging to all four groups competed with each other with a range of affinities for binding to $Gβ_1γ_2$, suggesting that all of the clones isolated from the phage display screen shared a common binding site on $Gβ_1γ_2$ (Scott, et al. (2001) supra).

Subsequent experiments have shown that not only does the SIRK peptide block heterotrimer formation, but it also displaces $Gα_{i1}$ from a $Gβ_1γ_2•Gα_{i1}$ complex in the absence of $Gα_{i1}$ activation and activates G protein-dependent ERK1 and ERK2 pathways in intact cells (Ghosh, et al. (2003) *J. Biol. Chem.* 278:34747-50; Goubaeva, et al. (2003) *J. Biol. Chem.* 278:19634-41). In vitro experiments revealed that SIRK facilitated nucleotide exchange-independent heterotrimer dissociation (Goubaeva, et al, (2003) supra; Ghosh, et al. (2003) supra) potentially explaining the activation of ERK in intact cells. Other Gβγ binding peptides such as QEHA, derived from adenylyl cyclase II (Weng, et al. (1996) *J. Biol. Chem.* 271:26445-26448; Chen, et al. (1997) *Proc. Natl. Acad. Sci. USA* 94:2711-2714) and amino acids 643-670 from the C-terminal region of βARK(GRK2) (Koch, et al. (1993) supra) could not promote dissociation of the hoterotrimer, despite competing for Gα subunit binding (Ghosh, et al. (2003) supra). This indicates that competition for Gα-Gβγ subunit binding is not sufficient for these peptides to accelerate subunit dissociation.

Using a doping mutagenesis and rescreening strategy, a peptide similar to the SIRK peptide was derived that had higher affinity for $Gβ_1γ_2$. The sequence of this peptide is Ser-Ile-Gly-Lys-Ala-Phe-Lys-Ile-Leu-Gly-Tyr-Pro-Asp-Tyr-Asp (SEQ ID NO:2) (SIGK). In vitro studies with the SIGK peptide indicate that it too can displace $Gα_{i1}$ from a heterotrimeric complex and also effectively prevents heterotrimer formation (Ghosh, et al. (2003) supra). The mechanism by which SIRK/SIGK mediates the dissociation of $G\alpha_{i1}$•GDP from $G\beta_1\gamma_2$ is not understood but was suggested to require a conformational change in $G\beta_1\gamma_2$ subunits to account for the enhanced $G\alpha_{i1}$ subunit dissociation rate in the presence of peptide (Ghosh, et al. (2003) supra).

SUMMARY OF THE INVENTION

The present invention relates to a method for identifying an agent that modulates at least one activity of a G protein. This method involves contacting a G protein β subunit with a test agent and determining whether the agent interacts with at least one amino acid residue of the protein interaction site of the β subunit thereby identifying an agent that modulates at least one activity of the G protein.

The present invention also relates to a method for identifying an agent that binds at least one amino acid residue of the protein interaction site of the β subunit. The method involves the steps of contacting a G protein β subunit with a test agent in the presence of a peptide that binds at least one amino acid residue of the protein interaction site of β subunit, and determining whether the agent inhibits the binding of the peptide to the at least, one amino acid residue of the protein interaction site of the β subunit thereby identifying an agent that binds at least one amino acid residue of the protein interaction site of the β subunit.

The present invention further relates to a method for modulating at least one activity of a G protein. This method involves contacting a G protein with an effective amount of an agent that interacts with at least one amino acid residue of the protein interaction site of the G protein β subunit so that at least one activity of the G protein is modulated.

The present invention is also a method for preventing or treating a disease or condition involving at least one G protein βγ subunit activity. The method involves administering to a patient having or at risk of having a disease or condition involving at least one G protein βγ subunit activity an effective amount of an agent that interacts with at least one amino acid residue of the protein interaction site of the G protein β subunit so that the at least one activity of the G protein is modulated thereby preventing or treating the disease or condition involving the at least one G protein βγ subunit activity. Diseases or conditions which involve G protein βγ subunit activities include heart failure, addiction, inflammation, and opioid tolerance.

A kit for identifying an agent that binds at least one amino acid residue of the protein interaction site of the β subunit is also provided. The kit of the invention contains a SIGK peptide or SIGK peptide derivative.

Agents identified in accordance with the screening methods of the present invention are further provided, wherein said agents have a structure of Formula I, II, or III.

BRIEF DESCRIPTION OF THE DRAWINGS

FIG. 5, comprising

DETAILED DESCRIPTION OF THE INVENTION

Figure 1:
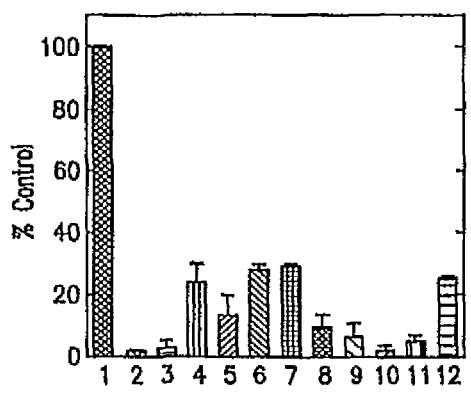
FIG. 1 is a graph illustrating that small molecules predicted to bind to the Gβ protein interaction site can interfere with peptide interactions at the protein interaction site. 1, control (DMSO); 2, NSC30820; 3, NSC12155; 4, NSC13984; 5, NSC117079; 6, NSC610930; 7, NSC293161; 8, NSC23128; 9, NSC402959; 10, NSC109268; 11, NSC125910; 12, SIGK in DMSO. 20 μM of SIGK and 200 μM of each small molecule were used in the assay.

The protein interaction site for G proteins has now been appreciated. The structure of Gβγ bound to SIGK was elucidated and indicates that SIGK binds to Gβγ as an α helix across the Gα interaction surface, in a position occupied by an α helical region of the switch II domain of Gα in the heterotrimer. The conformations of Gβγ in the presence and absence of SIGK are very similar. Thus, the crystal structure reveals how the peptide blocks Gα-Gβγ interactions. The structure further indicates that Gβ has evolved a highly reactive and specialized surface for interaction with diverse protein partners. This specialized surface is referred to herein as the "protein interaction site" or "protein interaction site of Gβ". Analysis of various characteristics of the protein interaction site led to the understanding that the basis for this surface as a preferred interaction surface is not an inherent conformational flexibility or unusually high surface accessibility of the site, but rather the prevalence of multiple types of potential interaction chemistries in this single binding surface. The specific amino acid combinations at this surface required for amino acid sequence recognition at the protein interaction site have also been determined. Moreover, the specific molecular interactions necessary for either acceleration of heterotrimer dissociation or inhibition of protein complex formation have been demonstrated.

Accordingly, the present invention relates to a method for identifying an agent that modulates (i.e., blocks or inhibits, or activates or potentiates) at least one activity of a G protein by contacting a G protein β subunit with a test agent (e.g., in a high-throughput screen) and determining whether the test agent interacts with at least one amino acid residue of the protein interaction site of the G protein β subunit. A G protein β subunit is intended to include any one of the five known mammalian G protein β subunit isoforms (Offermanns (2003) supra). An activity of a G protein is intended to mean the transduction of signals through the G protein to one or more downstream proteins including, but not limited to, G protein-regulated inward-rectifying potassium channel (GIRK); type I, type II, and type IV isoforms of adenylyl cyclase; mitogen-activated protein kinase (MAPK); phosphotidylinositol-3-kinase (PI3K); G protein receptor kinase (GRK) family members; and other plextrinhomology (PH) domain-containing proteins including the dynamins and the β1, β2, and β3 isoforms of phospholipase C β (PLC β). Modulation of G protein activity occurs via binding of the agent to at least one amino acid residue of the protein interaction site thereby blocking interactions between the Gβγ subunits and Gα subunit or the Gβγ subunits and the downstream proteins described herein.

The crystal structure of Gβγ₁ bound to SIGK revealed that the SIGK peptide interacts with residues of Gβ₁ subunit that are utilized by several Gβγ binding proteins (e.g., downstream proteins). For example, Lys57, Tyr59, Trp99, Met101, Leu117, Tyr145, Met188, Asp246, and Trp332 of Gβ₁ are involved in contacts with the GRK2 PH domain in the crystal structure of the Gβ₁γ₂•GRK2 complex, and all of these residues of Gβ₁ are involved in SIGK contacts as well (Table 1). This is in spite of the fact that the secondary structures of the PH domain that contact Gβ₁ (the RH-PH loop, the αCT region, and β4 strand) are completely dissimilar to the purely helical SIGK peptide (Lodowski, at al. (2003) supra). This theme is recapitulated in the complex of Gβ₁ with phosducin (Ford, et al. (1998) supra) where a common subset of Gβ₁ residues contacts a binding partner with different secondary structure from GRK2. Notably, the switch II region of Gα_{i1} forms an α-helix that is bound in almost the same orientation as the SIGK peptide. However, switch II of Gα_{i1} has no sequence similarity to the SIGK peptide, although it contains a lysine (Lys210) which is oriented in almost the same position as Lys4 of SIGK (Goubaeva, at al. (2003) supra).

TABLE 1

| Gα_{i1} | Phosducin | GRK2 | SIGK | PLCβ | AC | GIRK | Ca++ |
|---|---|---|---|---|---|---|---|
| 42 | | | | | | | |
| 44 | | | | | | | |
| 46 | | | | | | | |
| 47 | | | | | | | |
| 52 | | | | | | | |
| 53 | | | | | | | |
| 55 | | 55 | | | 55 | 55 | 55 |
| 57 | 57 | 57 | Lys57 | | 57 | | 57 |
| 59 | 59 | 59 | Tyr59 | | | 59 | |
| 75 | 75 | 75 | | | | | |
| | | 76 | | | | | |
| 78 | | 78 | | | 78 | 78 | 78 |
| 80 | | | | 80 | | 80 | |
| 88 | | | | | | | |
| 89 | | | | 89 | 89 | 89 | |
| 90 | | | | | | | |
| 91 | | | | | | | |
| 92 | | | | | | | |
| | | 95 | | | | | |
| | | 96 | | | | | |
| | 98 | 98 | | | | | |
| 99 | 99 | 99 | Trp99 | 99 | 99 | 99 | |
| | | | Val100 | | | | |
| 101 | 101 | 101 | Met101 | 101 | 101 | | 101 |
| 117 | 117 | 117 | Leu117 | 117 | 117 | | 117 |
| 119 | | | | 119 | 119 | | 119 |
| 132 | | | | | | | |
| 143 | | | | | 143 | | 143 |
| 144 | | | | | | | |
| 145 | 145 | 145 | Tyr145 | | | | |
| | 162 | | | | | | |
| 182 | | | | | | | |
| 186 | 186 | | Asp186 | 186 | 186 | | 186 |
| 188 | 188 | 188 | Met188 | | | | |
| 204 | 204 | 204 | | | | | |
| 228 | 223 | | Asp228 | 228 | 228 | 228 | 228 |
| 230 | 230 | | Asn230 | | | | |
| 246 | 246 | 246 | Asp246 | 246 | 246 | | |
| | 274 | | | | | | |
| | 290 | 290 | | | | | |
| | 292 | | | | | | |
| | 304 | | | | | | |
| | 310 | | | | | | |
| | 311 | | | | | | |
| | 314 | 314 | | | | | |
| 332 | 332 | 332 | Trp332 | 332 | 332 | | 332 |
| 41% | 44% | 44% | — | 54% | 67% | 43% | 60% |

Key to column headings: Gα_{i1}, the crystal structure of the Gα_{i1} · Gβ₁γ₂ heterotrimer (Wall, et al. (1995) supra; Wall, et al. (1998) supra); phosducin, the phosducin · Gβ₁γ₂ complex (Gaudet, et al. (1996) supra); GRK2, the GRK2 · Gβ₁γ₂ complex (Lodowski, et al. (2003) supra); SIGK, the SIGK · Gβ₁γ₂ complex; PLC β, mutational analysis of the PLC β2/3 · Gβ₁γ₂ complexes (Li, et al. (1998) supra; Ford, et al, (1998) supra); AC, mutational analysis of the adenylyl cyclase type I/II · Gβ₁γ₂ complex (Ford, et al. (1998) supra); GIRK, mutational analysis of Gβ₁γ₂ interaction with the GIRK1/4 channels (Ford, et al. (1998) supra); Ca++, mutational analysis of Gβ₁γ₂ interaction with N or P/Q type calcium channels (Ford, et al. (1998) supra; Agler, et al. (2003) J. Oen. Physiol. 121: 495-510).
Underlined residues indicate residues important for the SIGK · Gβ₁γ₂ interaction.
The last row indicates the percentage of residues that are shared between the target and the SIGK interfaces.

When mutational data for Gβγ targets PLC β2, adenylyl cyclase, and GIRK and CCα1B calcium channels are included in this analysis, the footprint of SIGK upon. Gβ is similar to the footprints of these former targets (Li, et al. (1998) supra; Ford, et al, (1998) supra). Of the thirteen residues from Gβ that encompass the protein interaction site, nine (Lys57, Tyr59, Trp99, Met101, Leu117, Tyr145, Met188, Asp246, and Trp332) are also found as contacting residues in the Gα, GRK2, and phosducin complexes (Table 1). These residues reflect a consensus set of residues utilized by many Gβ binding partners. An additional three of the thirteen residues (Asp186, Asp228, and Asn230) are shared amongst SIGK and two of the other protein complex structures. One of the thirteen, Val100, contacts SIGK through its main chain oxygen and is not involved in binding interactions in the other complexes. The SIGK binding residues that are most sensitive to mutational perturbation are also the most frequently involved in interactions with other Gβ binding partners. SIGK was identified from a random peptide phage display where multiple peptides, unrelated by sequence, appeared to bind to a common protein interaction site on Gβ₁.

Because of the extensive overlap between the residues of Gβ₁ that are accessed by SIGK and those involved in the binding of protein Gβγ targets, SIGK is a competitive inhibitor of multiple Gβγ binding reactions. The closely related SIRK peptide has effects on several Gβγ-dependent pathways; it blocks Gβγ-mediated activation of PLC β2, PLC β3 and PI3K in enzyme assays, and induces ERK I/II activation in a cell-based assay (Scott, et al. (2001) supra; Goubaeva, et al. (2003) supra). These effects are sensitive to mutations of residues in SIGK that interact with the surface of Gβ, as Lys4, Ala5, Phe6, Ile8, Leu9, and Gly10 of SIGK have all been shown by alanine scanning to be important for inhibition of PLC β2 activation by Gβ₁γ₂ (Scott, et al. (2001) supra). In addition, Leu9 of SIGK is important for the ability of SIGK to activate MAPK pathways in cell culture (Goubaeva, et al. (2003) supra). However, SIRK does, not block inhibition of adenylyl cyclase type I or N-type $Ca^{2+}$ channel regulation, even though their footprints are quite similar to those of Gα and PLC β2 (Scott, et al. (2001) supra). Conversely, mutations in Gβ that abrogate SIGK binding do not equally affect interaction with other Gβγ binding partners. For example, mutation of Leu117 to alanine decreases the ability of Gβ₁γ₂ to activate adenylyl cyclase type II and PLC β3 and to bind GRK2 and SIGK, but has no effect on GIRK1/GIRK4 potassium channel activation, CCα1B calcium channel activation, or PLC β2 activation (Table 1) (Li, et al. (1998) supra; Ford, et al. (1998) supra). Similarly, mutation of Trp332 of Gβ₁γ₂ to alanine reduces affinity of Gβ₁γ₂ for SIGK and impairs stimulatory activity towards adenylyl cyclase type II, CCα1B and both PLC β2 and PLC β3, but does not affect interaction with GRK2, activation of GIRK1/GIRK4, or inhibition of adenylyl cyclase type I (Li, et al. (1998) supra; Ford, et al. (1998)

supra). Both Leu117 and Trp332 of Gβ$_1$γ$_2$ form part of the Gα$_t$ and Gα$_{i1}$ binding sites of Gβ$_1$ (Wall, et al. (1995) supra; Lambright, et al. (1996) supra; Wall, et al. (1998) supra) and mutation of Leu117 also affects Gα$_{i1}$ association with Gβ$_1$γ$_2$ (Li, et al. (1998) supra; Ford, et al. (1998) supra).

Unlike other peptides that block heterotrimer formation (Ghosh, et al. (2003) supra), SIGK promotes nucleotide exchange-independent dissociation of Gβ$_1$γ$_2$ from Gα$_{i1}$ (Ghosh, et al. (2003) supra; Goubaeva, et al. (2003) supra). For example, a peptide derived from the C-terminus of GRK2 blocks heterotrimer formation (Ghosh, et al. (2003) supra) but does not promote Gα$_{i1}$•Gβ$_1$γ$_2$ subunit dissociation, even though the structure of the GRK2•Gβ$_1$γ$_2$ complex indicates that this peptide should utilize much the same surface of Gβ$_1$ as SIGK (Lodowski, et al. (2003) supra). Not to be bound by theory, SIGK could promote heterotrimer dissociation by either of two mechanisms. SIGK may induce conformational changes on Gβ$_1$ that propagate beyond the SIGK binding site and disrupt other interactions between Gβ$_1$ and Gα$_{i1}$. However, the Gβ$_1$γ$_2$•SIGK structure shows that SIGK does not induce substantial conformational change in Gβ$_1$ outside of the SIGK binding site itself. The second mechanism relies on the assumption that Gα$_{i1}$ can dynamically detach from and rebind to either of two surfaces on Gβ: the switch II interaction site on the top face of Gβ$_1$, where SIGK binds in a similar orientation, and the N-terminal interaction surface on blade one of Gβ$_1$. Transient release from Gα$_{i1}$ at the switch II interface would allow SIGK access to Gβ$_1$. Complete release of Gα$_{i1}$ from Gβ could then occur if the off-rate for SIGK is slower than that for dissociation of the N-terminus of Gα$_{i1}$. Thus the GRK2 peptide, which binds the top surface of Gβ, may dissociate too quickly to promote dissociation of Gα. This dynamic model of Gβγ interactions is biologically relevant, since many Gβγ binding targets exhibit binding outside of the top surface of Gβ and may also transiently sample alternate surfaces on Gβ.

The ability of the protein interaction site of Gβ$_1$γ$_2$ to recognize a range of protein ligands with diverse secondary structures indicates that it may be an example of a preferential protein binding site (see, e.g., Delano, et al. (2000) *Science* 287:1279-1283). Preferential binding surfaces are characterized as having high solvent accessibility, low polarity, and a large degree of conformational flexibility (Scott, et al. (2001) supra; Ma, et al. (2001) *Curr. Opin. Struct. Biol.* 11:364-9; Bogan and Thorn (1998) *J. Mol. Biol.* 280:1-9; Clackson and Wells (1995) *Science* 267:383-6; DeLano (2002) *Curr. Opin. Struct. Biol.* 12:14-20). Moreover, preferential binding sites are likely to contain an unusually high concentration of so-called "hot spots", i.e., residues that, if mutated to alanine, reduce binding energy at least ten-fold (DeLano (2002) supra). Hot spots have been described for both protein-protein and protein-small molecule interfaces; often point mutations to any hot spot on a surface completely abrogate complex formation, even when the binding interfaces bury several hundred Å2 of total surface area (Bogan and Thorn (1998) supra; Clackson and Wells (1995) supra; Thanos, et al. (2003) *J. Am. Chem. Soc.* 125:15280-1; Zhang, et al. (2003) *J. Biol. Chem.* 278:33097-104). These criteria have been used herein to evaluate the protein interaction site of Gβ$_1$ as a protein surface that is predisposed by its chemical composition and surface properties to serve as a protein binding site. Of the twelve residues in the protein interaction site of Gβ, eight (Lys57, Tyr59, Leu117, Tyr145, Asp186, Met188, Asn230, and Trp332) met the energetic criterion for a hot spot residue. Replacement of any of these residues by alanine resulted in a 10-fold reduction in the affinity of Gβ$_1$γ$_2$ for SIGK. It is clear that all of these residues act as energetically important nodes that contribute favorably to SIGK binding. The SIGK binding surface of Gβ$_1$ contains several residues that have been shown to be enriched in hot spots (Bogan and Thorn (1998) supra). These include tyrosine, tryptophan and arginine; bulky residues that are capable of forming both polar and non-polar interactions. The protein interaction site of Gβ is significantly more populated with aromatic residues than the rest of the Gβ surface. 38% of the SICK binding surface versus 8.5% of the total non-glycine surface accessible Gβ residues is composed of Phe, Tyr, His, or Trp. Therefore, the protein interaction site of Gβ is more nonpolar; in total, 62% of the protein interaction site of Gβ is nonpolar compared to 29% of Gβ surface accessible residues. Further, asparagine and aspartic acid, which have a moderately favorable distribution among hot spot surfaces, account for four of the thirteen residues in the protein interaction site of Gβ. This combination of aromatic and charged residues allows for accommodation of binding partners with diverse chemical properties at the Gβ protein interaction site. Preferential binding surfaces are expected to have high surface accessibility (DeLano, et al. (2000) supra). To analyze this property of the protein interaction site of Gβ, the total surface accessible area was calculated for the Gβ molecule on a residue, main chain, and side chain basis. Most amino acids in the protein interaction site of Gβ were not significantly more accessible than others of their type in Gβ. However, five residues showed significant deviation from the mean: Tyr59, Trp99, Met101, Leu117, and Trp332. In the case of Trp99, side chain surface accessibility was significantly greater than the type average; the main chain of Tyr59, Trp99, and Met101 were more accessible than the mean. Leu117 had significantly higher main chain and side chain accessibility than the mean.

Conformational flexibility or adaptability has been cited as an important determinant of a preferential binding surface, since such surfaces are better able to bind to structurally unrelated protein targets (DeLano, et al. (2000) supra). Residue flexibility can be quantified in terms of relative positional variation in the context of several protein complexes. Histogram analysis of the RMSD relative to uncomplexed Gβ$_1$γ$_1$ of all Gβ residues in four crystal structures (Gβ$_1$γ$_2$•SIGK; Gβ$_1$γ$_2$•Gα$_{i12}$; Gβ$_1$γ$_2$•GRK2; Gβ$_1$γ$_1$•phosducin) shows that the protein interaction site residues of Gβ exhibit only slightly greater than average side chain positional dispersity (1.42 Å compared to 1.35 Å), with the side chains of Trp99, Asp228, and Trp332 having the largest positive deviation from the average (each greater than 2 Å). In particular, Arg314 and Trp332 in blade seven move more than 10 Å towards the outside of the Gβ$_1$ torus to interact with phosducin. Atomic B factors also provide a measure of conformational flexibility. In the structure of uncomplexed Gβ$_1$γ$_1$ the B factors for Trp99, Val100, and Met101 exceed the mean value by least one standard deviation (Trp99 is greater than two standard deviations from the mean). In complexes with Gα$_{i1}$, GRK2, phosducin, and SIGK complexes, these binding site residues become more well-ordered with B values close to the mean and in some cases up to one standard deviation below the mean. Thus, the capacity of Gβ to recognize structurally diverse binding partners does not require a high degree of conformational flexibility for most residues in the protein interaction site of Gβ. Small structural adaptations in Gβ$_1$ are sufficient to accommodate a range of co-evolving binding partners. Structural and mutagenic analysis demonstrates that the protein interaction site on Gβ can be regarded as a hot surface, co-evolved to promote tight binding with multiple protein targets. However, the mechanism by which Gβγ acts as a hot surface is complex. Trp332 is the only residue which meets all four of the criteria for a hot spot, although Tyr59 and Trp99 have three of the four characteristics of hot spot residues that were tested. There are other residues in the top face of Gβ that are sensitive to mutational perturbation and are utilized in many binding partner interactions but do not exhibit the characteristics of conformational flexibility, solvent accessibility, or nonpolarity expected of hot spots. Especially notable among this group are Lys57 and Met188; both of these residues are energetically significant binding determinants in Gβ as shown by mutational analysis and comparison to known Gβγ complex structures, and yet do not meet any of the additional Statistical criteria for hot spot residues.

Accordingly, an amino acid residue of the protein interaction site of a Gβ is intended to include Lys57, Tyr59, Trp99, Val100, Met101, Leu117, Tyr145, Asp186, Met188, Asp228, Asn230, Asp246, and Trp332. By way of illustration, the location of these residues is provided in the rat Gβ amino acid sequence of:

MGEMEQLKQE AEQLKKQIAD ARKACADITL
AELVSGLEVV GRVQMRTRRT LRGHLAKIYA
MHWATDSKLL VSASQDGKLI VWDTYTTNKV
HAIPLRSSWV MTCAYAPSGN FVACGGLDNM
CSIYSLKTRE GNVKVSRELS AHTGYLSCCR
FLDDNNIVTS SGDTTCALWD IETGQQKTVF
VGHTGDCMSL AVSPDYKLFI SGACDASAKL
WDVREGTCRQ TFTGHESDIN AICFFPNGEA
ICTGSDDASC RLFDLRADQE LTAYSHESII
CGITSVAFSL SGRLLLAGYD DFNCNVWDSL
KCERVGVLSG HDNRVSCLGV TADGMAVATG S
WDSFLKIWN (GENBANK Accession No. AAA62620; SEQ ID NO:3), wherein the protein interaction site residues are underlined.

Likewise, these residues are located in the same position in a human Gβ having the amino acid sequence of:

MSELEQLRQE AEQLRNQIRD ARKACGDSTL
TQITAGLDPV GRIQMRTRRT LRGHLAKIYA
MHWGTDSRLL VSASQDGKLI IWDSYTTNKV
HAIPLRSSWV MTCAYAXSGN FVACGGLDNI
CSIYSLKTRE GNVRVSRELP GHTGYLSCCR
FLDDNQIITS SGDTTCALWD IETGQQTVGF
AGHSGDVMSL SLAPNGRTFV SGACDASIKL
WDVRDSMCRQ TFIGHESDIN AVAFFPNGYA
FTTGSDDATC RLFDLRADQE LLMYSHDNII
CGITSVAFSR SGRLLLAGYD DFNCNIWDAM
KGDRAGVLAG HDNRVSCLGV TDDGMAVATG S
WDSFLKIWN (GENBANK Accession No. AAA35922; SEQ ID NO:4), wherein the protein interaction site residues are underlined.

An agent which interacts with at least one of these amino acid residues of the protein interaction site of Gβ can bind via various heterogeneous non-bonded interactions including, but not limited to van der Waals contacts (e.g., with methionine or leucine), polar contacts (e.g., with aspartate or asparagine), or both (e.g., with lysine, tryptophan, or tyrosine) to contribute to the energy of binding. In general, it is desirable that the agent interacts with 2, 3, 4, 5, 6, 7, 8, 9, 10, 11, 12 or 13 of the amino acid residues of the protein interaction site of Gβ to enhance the specificity of the agent for one or more G protein interacting proteins and therefore one or more G protein-mediated signaling pathways.

Determining whether the agent interacts with at least one amino acid residue of the protein interaction site of the β subunit can be accomplished using various in vitro or in vivo assays based on detecting protein-protein interactions between the Gβγ subunits and other peptides or proteins known to interact with Gβγ subunits (e.g., SICK peptide, Gα subunit, or downstream proteins). An exemplary in vitro assay has been disclosed herein. This assay consists of obtaining an isolated Gβγ complex; contacting the Gβγ complex with a test agent in the presence of a peptide that binds at least one amino acid residue of the protein interaction site of β subunit, (e.g., a SICK peptide or SICK peptide derivative of SEQ ID NO:1, SEQ ID NO:2, SEQ ID NO:5, SEQ ID NO:6, SEQ ID NO:7, SEQ ID NO:8, SEQ ID NO:9, SEQ ID NO:10, SEQ ID NO:11, SEQ ID NO:12, or SEQ ID NO:13); and detecting the ability of the agent to inhibit the binding of the peptide to the protein interaction site of the β subunit using, for example, an ELISA assay. Other phage displayed peptides identified in the original screen (Scott, et al. (2001) supra) could also be used.

Alternatively, an in vivo assay can be used to determine whether a test agent interacts with at least one amino acid residue of the protein interaction site of the β subunit. By way of illustration, a two-hybrid assay is contemplated where the test agent is contacted with a cell expressing Gβγ subunits and a peptide such as SIGK, wherein the β subunit is fused to, e.g., a DNA-binding domain and the SIGK peptide is fused to an activation domain. When the SIGK peptide is bound to the protein interaction site of Gβγ, reporter protein expression is induced. If the test agent disrupts the binding of the SIGK peptide to the protein interaction site of Gβγ, reporter protein expression is blocked.

Additional screens such as well-established computational screens or screens that detect the activity of G protein-dependent downstream proteins (e.g., PLC β enzymatic activity) are also contemplated for use in conjunction with the assays disclosed herein.

Test agents, also referred to herein as compounds, which can be screened in accordance with the methods of the present invention are generally derived from libraries of agents or compounds. Such libraries can contain either collections of pure agents or collections of agent mixtures. Examples of pure agents include, but are not limited to, proteins, polypeptides, peptides, nucleic acids, oligonucleotides, carbohydrates, lipids, synthetic or semi-synthetic chemicals, and purified natural products. Examples of agent mixtures include, but are not limited to, extracts of prokaryotic or eukaryotic cells and tissues, as well as fermentation broths and cell or tissue culture supernates. In the case of agent mixtures, the methods of this invention are not only used to identify those crude mixtures that possess the desired activity, but also provide the means to monitor purification of the active agent from the mixture for characterization and development as a therapeutic drug. In particular, the mixture so identified can be sequentially fractionated by methods commonly known to those skilled in the art which can include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

Library screening can be performed as exemplified herein or can be performed in any format that allows rapid preparation and processing of multiple reactions. Stock solutions of the test agents as well as assay components are prepared manually and all subsequent pipeting, diluting, mixing, washing, incubating, sample readout and data collecting is done using commercially available robotic pipeting equipment, automated work stations, and analytical instruments for detecting the signal generated by the assay. Examples of such detectors include, but are not limited to, luminometers, spectrophotometers, and fluorimeters, and devices that measure the decay of radioisotopes.

To further evaluate the efficacy of a compound identified using a screening method of the invention, one of skill will appreciate that a model system of any particular disease or disorder involving G protein signaling can be utilized to evaluate the adsorption, distribution, metabolism and excretion of a compound as well as its potential toxicity in acute, sub-chronic and chronic studies. For example, overexpression of βγ inhibitors in NG108-15/D2 cells and rat primary hippocampal neurons has been shown to block δ-opioid and cannabinoid receptor-induced PKA Cα translocation and gene expression by preventing βγ activation of adenylyl cyclase (Yao, et al. (2003) *Proc. Natl. Acad. Sci. USA* 100: 14379-84). Accordingly, to analyze the efficacy of a compound of the instant invention for treating addiction, NG108-15/D2 cells and/or rat primary hippocampal neurons are contacted with said compound and the effect on PKA Cα translocation is determined. Compounds which block δ-opioid and cannabinoid receptor-induced PKA Cα translocation will be useful in treating addiction.

Efficacy of compounds of the instant invention for preventing or treating heart failure can be analyzed in a genetic model of murine-dilated cardiomyopathy which involves the ablation of a muscle-restricted gene that encodes the muscle LIM protein (MLP$^{-/-}$) (Arber, et al. 1997) *Cell* 88:393-403). Using this model, it has been demonstrated that a beta-adrenergic receptor kinase 1 inhibitor, BARK-ct, which binds to βγ and blocks βγ-dependent activation of beta-adrenergic receptor kinase 1 activity, can enhance cardiac contractility in vivo with or without isoproterenol (Koch, et al. (1995) *Science* 268:1350-3) and restore left ventricular size and function (Rockman, eta 1. (1998) *Proc. Natl. Acad. Sci.* 95:7000-7005). Similarly, compounds of the instant invention which block βγ-dependent activation of beta-adrenergic receptor kinase 1 activity will be useful in preventing or treating heart failure.

The effectiveness of compounds of the instant to prevent opioid tolerance can be analyzed in acute (Jiang, et al. (1995) *J. Pharmacol. Exp. Ther.* 273:680-8) and chronic (Wells, et al. (2001) *J. Pharmacol. Exp. Ther.* 297:597-605) dependence model systems, wherein mice are injected intracerebroventricularly with a compound of the instant invention and tolerance to a select opioid (e.g., morphine) is determined. Compounds which decrease the amount of opioid necessary to achieve an analgesic effect will be useful in preventing opioid tolerance.

PLC-β2 and -β3 and PI3Kγ have been shown to be involved in the chemoattractant-mediated signal transduction pathway. Mice deficient in PI3Kγ lack neutrophil production of PtdIns(3,4,5)P$_3$, neutrophil migration, and production of antibodies containing the λ chain when immunized with T cell-independent antigen hydroxylnitrophenyl-FICOLL™ (Li, et al. (2000) *Science* 287:1046-1049). Mice lacking PLC-β2 and -β3 are deficient in Ca$^{2+}$ release, superoxide production, and MAC-1 up-regulation in neutrophils (Li, et al. (2000) supra). Further, PLC-β2 deficient mice exhibit enhanced chemotaxis of different leukocyte populations and are sensitized to bacteria, viruses, and immune complexes (Jiang, et al. (1997) *Proc. Natl. Acad. Sci. USA* 94(15):7971-5). Accordingly, to analyze the efficacy of a compound of the instant invention for modulating an inflammatory response, mice can be administered said compound and the effect on neutrophil production of PtdIns(3,4,5)P$_3$, neutrophil migration, Ca$^{2+}$ efflux, superoxide production, production of antibodies containing the λ chain when immunized with T cell-independent antigen hydroxylnitrophenyl-FICOLL™ is determined. Compounds which selectively potentiate PLC-β2 and -β3 and/or block PI3Kγ activation thereby inhibiting production of PtdIns(3,4,5)P$_3$, neutrophil migration, and production of TI-Igλ$_L$, will be useful in treating inflammatory conditions such as arthritis, allergies, Chrohn's Disease and the like. Compounds which selectively block, e.g., PLC-β2 activation thereby facilitating neutrophil migration will be useful in facilitating immune responses to bacterial and viral infections.

Using the screening method of the present invention, various compounds have now been identified which bind to the protein interaction site of a Gβ subunit to interfere with or potentiate physiologically relevant protein interactions (e.g., Gα subunit and PLC β interactions) thereby modulating the activity of G protein signaling pathways.

Accordingly, one embodiment of the present invention is a compound having a structure of Formula I:

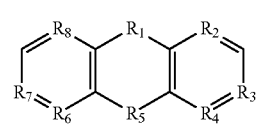

FORMULA I

Exemplary compounds having the structure of Formula I which depict various substituent R groups include, but are not limited to, the following:

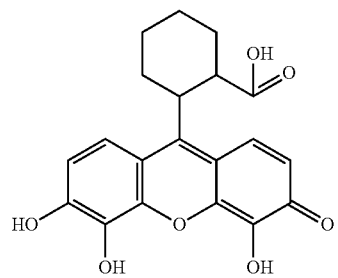

NSC119910

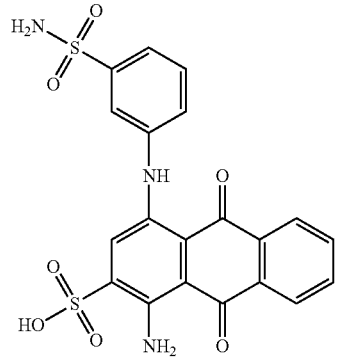

NSC117079

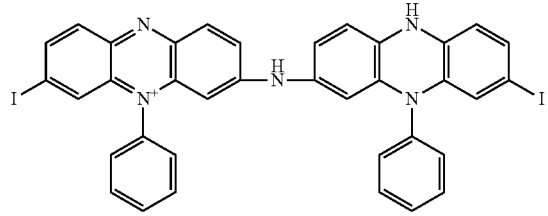

NSC402959

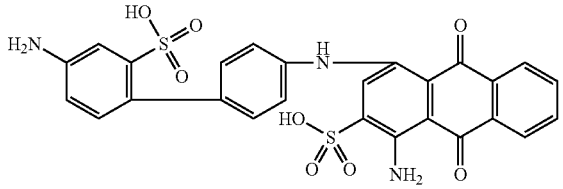

NSC125910

-continued

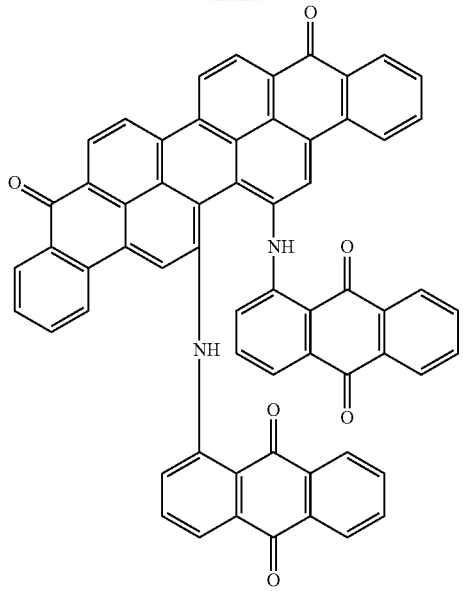

NSC23128 and pharmaceutically acceptable salts and complexes thereof.

Another embodiment of the present invention is a compound having a structure of Formula II:

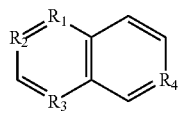

FORMULA II

Exemplary compounds having the structure of Formula II which depict various substituent R groups include, but are not limited to, the following:

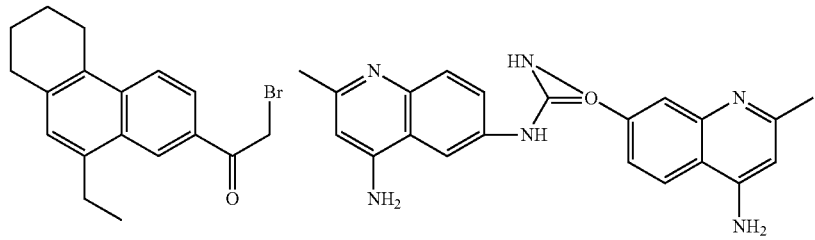

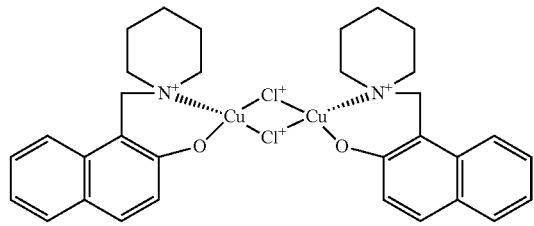

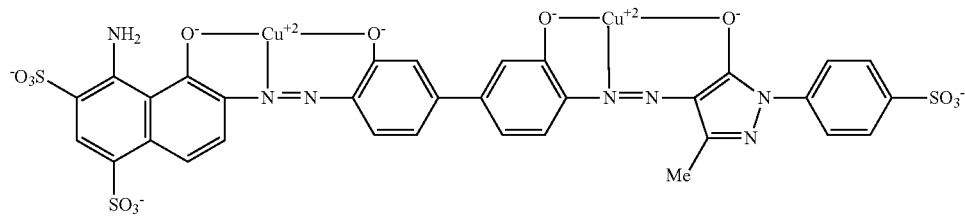

and pharmaceutically acceptable salts and complexes thereof.

Additional exemplary compounds which bind to the protein interaction site of Gβ include, but are not limited to, the following:

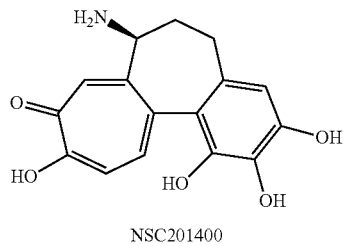

NSC201400

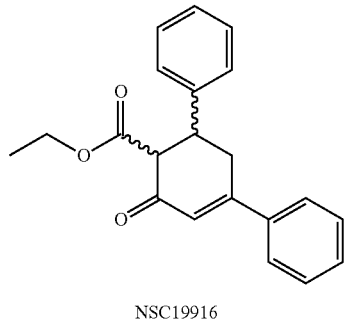

NSC19916 and pharmaceutically acceptable salts and complexes thereof.

Exemplary compounds disclosed herein are intended to include all enantiomers, isomers or tautomers, as well as any derivatives of such compounds that retain the same biological activity as the original compound.

Exemplary compounds of the present invention were initially selected from a computational screen to identify ligands that bind to the novel protein interaction site of Gβ. The computational screen involved using SYBYL molecular modeling software to model the protein interaction site of Gβ as determined in the X-ray structure disclosed herein. The computational docking screen was performed with the National Cancer Institute 1900 compound library wherein the compounds were tested for docking to the protein interaction site of Gβ using FLEXX™ (Tripos, Inc., St. Louis, Mo.) for docking and CSCORE™ (Tripos, Inc.) to evaluate the energetics and fitness of the docked structure. Algorithm-dependent lists of compounds, predicted to interact with the protein interaction site of Gβ and the structural model of the interaction, were generated. Selected compounds were subsequently analyzed in the phage ELISA binding assay disclosed herein to assess whether these compounds could bind to the protein interaction site of Gβ and interfere with protein interactions at this surface. Compounds NSC201400 and NSC119916 had $IC_{50}$ values of 100 nM and 5 μM, respectively, and the remaining compounds were found to bind in the ELISA-based assay to Gβγ with an affinity of at least 50 μM and interfere with peptide interactions at the protein interaction site (FIG. 1). These compounds were further analyzed in the phage ELISA assay and found to have high affinities for the protein interaction site of Gβ and interacted with similar amino acid residues as SIGK.

TABLE 2

| SIGK | NSC30820 | NSC12155 | NSC117079 | NSC23128 | NSC402959 | NSC109268 |
|---|---|---|---|---|---|---|
| Lys57 | Lys57 | | | Lys57 | Lys57 | |
| Tyr59 | Tyr59 | | | Tyr59 | Tyr59 | |
| | Gln75 | | | Gln75 | | |
| Trp99 | Trp99 | | | Trp99 | Trp99 | |
| Val100 | | | | | | |
| Met101 | | | | | | |
| Leu117 | | | | | Leu117 | |
| Tyr145 | | | | | | |
| Asp186 | | | | | | |
| Met188 | | | | | | |
| | | | | | | Cys204 |
| Asp228 | | | | | | Asp228 |
| Asn230 | | Asn230 | Asn230 | | | Asn230 |
| Asp246 | | Asp246 | | | | Asp246 |
| | | Thr274 | | | | |
| | | | Arg314 | | | Arg314 |
| Trp332 | | | | | | |
| $IC_{50}$ | 100 nM | 13 μM | 43 μM | 16 μM | 2 μM | 13 μM |

| SIGK | NSC125910 | NSC119910 | NSC30671 |
|---|---|---|---|
| Lys57 | | Lys57 | Lys57 |
| Tyr59 | Tyr59 | Tyr59 | Tyr59 |
| Trp99 | Trp99 | Trp99 | Trp99 |
| Val100 | | Val100 | |
| Met101 | | Met101 | |
| Leu117 | Leu117 | Leu117 | |
| Tyr145 | | | |
| Asp186 | | | |
| Met188 | | | Met188 |
| | | | Cys204 |
| Asp228 | | | Asp228 |
| Asn230 | | | |
| Asp246 | | | |
| | Thr274 | | |
| | | Ser316 | |
| Trp332 | Trp332 | Trp332 | |
| $IC_{50}$ | 68 μM | 100 nM | 7 μM |

Underlined residues indicate residues important for the SIGK · Gβ₁γ₂ interaction.
The last row indicates the $IC_{50}$ value for each compound.

Figure 2:
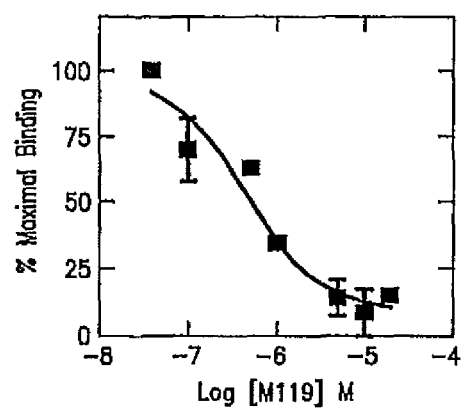
FIG. 2 is a graph illustrating that NSC119910 binds to Gβγ and interferes with physiologically relevant protein interactions such as with the Gα subunit.
Figure 3:
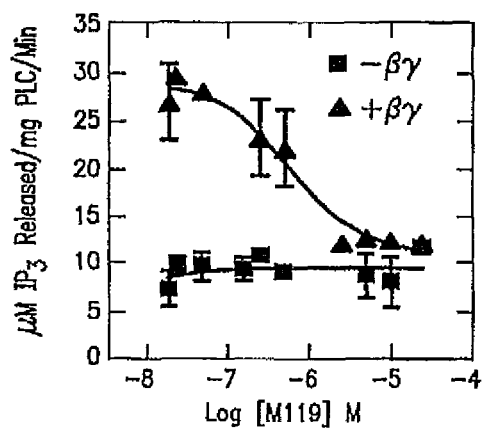
FIG. 3 is a graph illustrating the inhibition of phospholipase C-Gβγ interactions by NSC119910. Phospholipase enzymatic activity was determined using well-established methods (Ghosh and Smrcka (2003) Meth. Mol. Biol. 237: 67-75).

To further illustrate the utility of these compounds, it was demonstrated that NSC119910 blocked interactions of Gα subunit with Gβγ subunits (FIG. 2) and inhibited the ability of Gβγ subunits to inhibit interactions with a physiological target such as PLC β in vitro (FIG. 3) based on a decrease in the enzymatic activity of PLC β.

Figure 4:
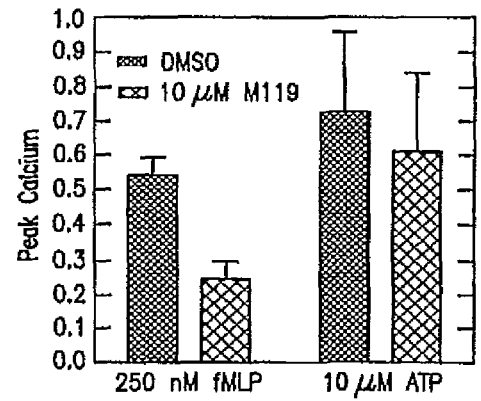
FIG. 4 is a bar graph depicting the peak cytosolic $Ca^{2+}$ concentrations for neutrophils activated with fMLP or ATP agonists in the presence or absence of 10 μM NSC119910. fMLP, n=3; ATP, n=2.
Figure 5A:
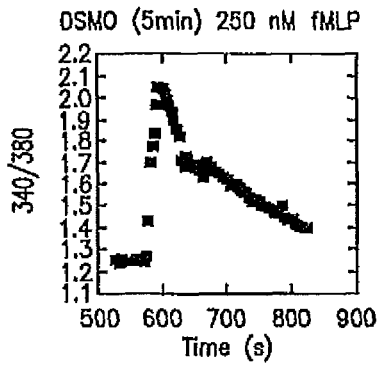
FIGS. 5A-5D, is a series of graphs illustrating representative experiments demonstrating peak cytosolic $Ca^{2+}$ concentrations, as well as the time taken for fluorescence intensity to decline to half-peak ($t_{1/2}$) values, for neutrophils activated with fMLP (FIGS. 5A-B) or ATP (FIGS. 5C-D) in the absence (FIGS. 5A and 5C) and presence (FIGS. 5B and 5D) of 10 μM NSC119910.
Figure 5B:
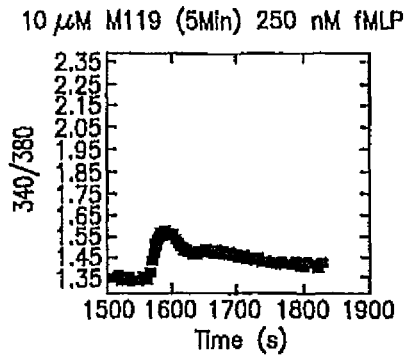
Figure 5C:
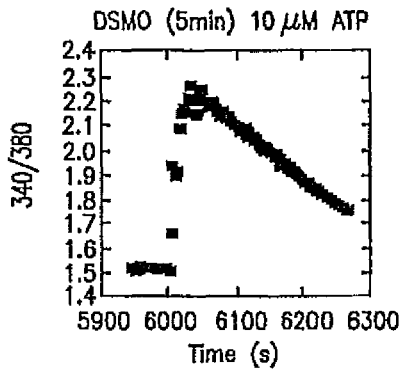
Figure 5D:
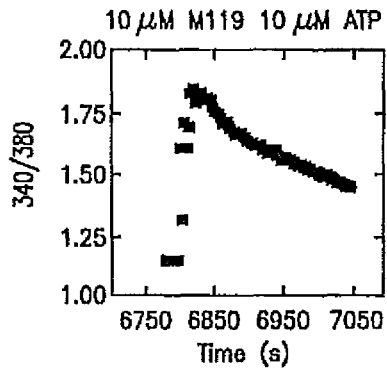

Gβγ-regulated activities of PI3Kγ and PLC-β2/-β3 are important in chemoattractant-induced responses and inflammation. PI3Kγ is involved in the production of TI-Ig$\lambda_L$ and mice deficient in PI3Kγ, lack neutrophil migration (Li, et al, (2000) *Science* 287:1046-9). The PLC pathway is involved in down-modulation of chemotaxis and in hyperinflammatory conditions (Li, et al. (2000) supra). Therefore, it was determined whether NSC119910 could inhibit the Gβγ/PLC interaction and block PLC activation. Data from fury-2-based experiments demonstrated that the abruptly occurring increase in cytosolic $Ca^{2+}$ in fMLP-stimulated neutrophils, a response which is due to the release of the cation from intracellular stores (Anderson, and Mahomed (1997) *Clin. Exp. Immunol.* 110:132-138; Geiszt, et al. (1997) *J. Biol. Chem.* 272:26471-26478), was suppressed by 10 µM NSC119910 (FIG. 4). Increases in [$Ca^{2+}$] through ATP was not significantly suppressed in the presence of NSC119910 (FIG. 4), indicating that the effect of the compound on fMLP dependent $Ca^{2+}$ increases are specific. Further, the time taken for fluorescence to decline to half-peak values was not substantially affected (FIG. 5). The results indicate that NSC119910 inhibits PLC/G-protein interactions which lead to activation of PLC in vivo.

Opioid receptors, µ, Δ, and κ, couple to $G_i$ and $G_o$ proteins through α and βγ subunits, and regulate a number of signaling pathways. In particular, the efficacy of opioid signal transduction in PLC-β3-deficient mice has been shown to increase, indicating that PLC suppresses opioid signaling by modification of opioid-dependent signaling components (Xie, et al. (1999) *Proc. Natl. Acad. Sci. USA* 96:10385-10390). Given that PLC-β3 plays a significant role as a negative regulator of opioid responses, it was determined whether NSC119910 could inhibit PLC-β3 activation thereby enhancing morphine-induced analgesia. Mice were intracerebroventricularly injected in accordance with standard protocols (Xu, et al. (1998) *J. Pharmacol. Exp. Therapeut.* 284:196-201) with 100 nmol of NSC119910 in combination with varying doses (0.1, 0.3, 1, and 3 nmol) of morphine. Mice were tested 20 minutes after the injection for an analgesic response in a 55° C. warm-water tail-flick test (Wells, et al. (2001) *J. Pharmacol. Exp. Therapeut.* 297:597-605). The $ED_{50}$ value for morphine alone was 0.74 nmol, while the $ED_{50}$ value for NSC119910 plus morphine was 0.065 nmol. The differences in the $ED_{50}$ values showed an 11-fold shift to the left in a morphine dose-response curve (Table 3), indicating that when morphine was administered with NSC119910, less morphine was required to produce a similar analgesic effect. Accordingly, administering (opioids in combination with a compound of the instant invention would allow for the use of a lower dose of opioid in patients thereby reducing the development of opioid tolerance.

TABLE 3

| Dose of Morphine, nmol | Percent Antinociception ± S.E.M. | |
|---|---|---|
| | Morphine Alone | Morphine plus NSC119910 |
| 10 | 82.4 ± 11.9 | N/A |
| 3 | 68.0 ± 14.1 | 100 ± 0.0 |

TABLE 3-continued

| Dose of Morphine, nmol | Percent Antinociception ± S.E.M. | |
|---|---|---|
| | Morphine Alone | Morphine plus NSC119910 |
| 1 | 55.6 ± 8.3 | 79.3 ± 9.1 |
| 0.3 | 41.0 ± 10.2 | 64.4 ± 10.0 |
| 0.1 | 21.0 ± 11.1 | 55.3 ± 12.7 |

Having demonstrated that NSC119910 effectively modulates G-protein interactions, a series of structural analogs of NSC119910, identified using modeling software, were analyzed for binding to the protein interaction site of Gβ. These analogs and their corresponding affinities for Gβγ were:

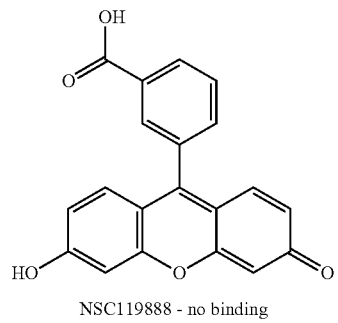

NSC119888 - no binding

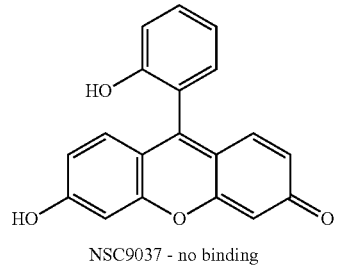

NSC9037 - no binding

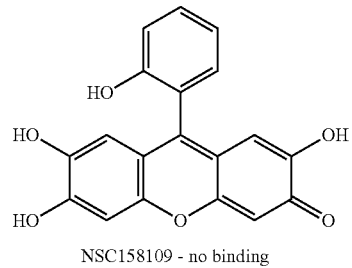

NSC158109 - no binding

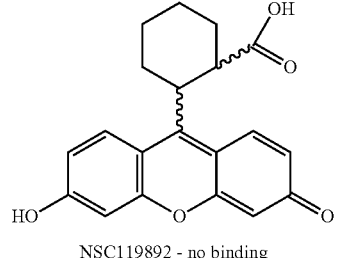

NSC119892 - no binding

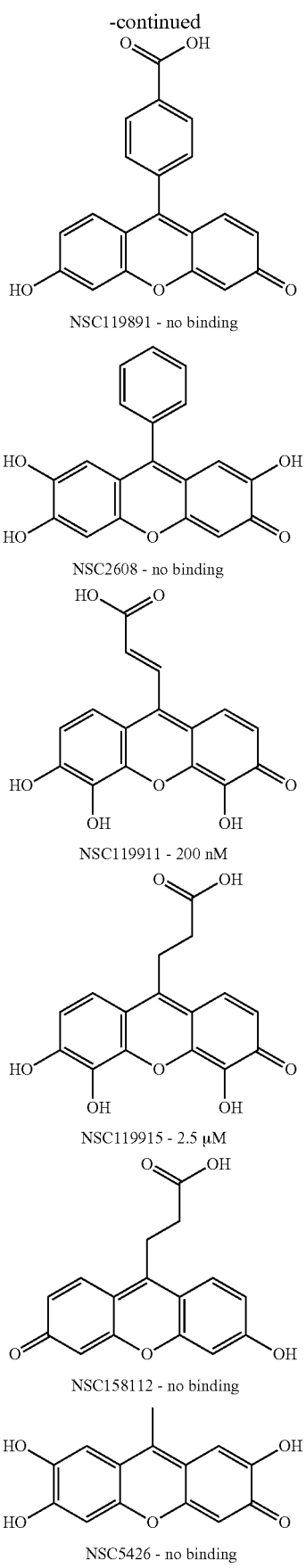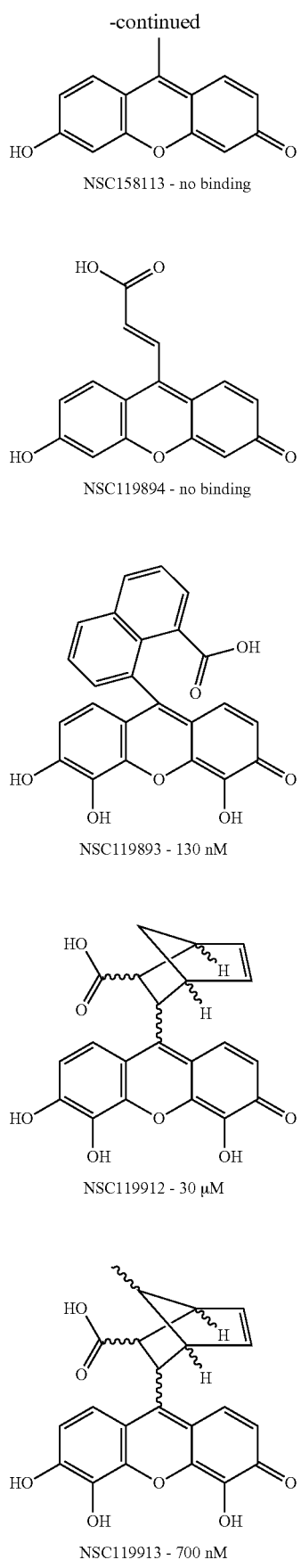

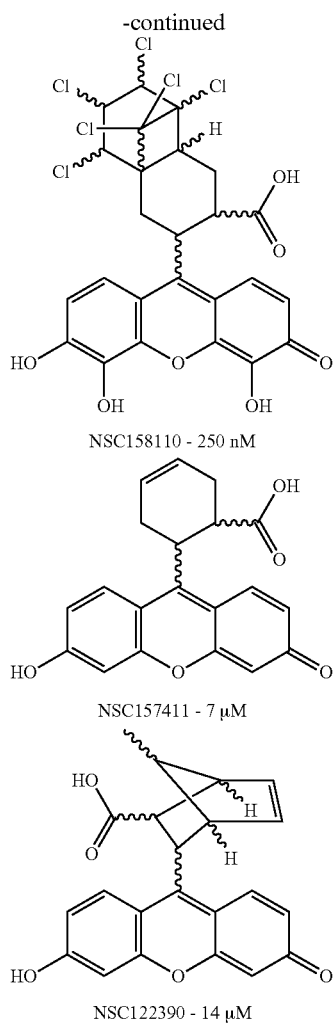

NSC158110 - 250 nM

NSC157411 - 7 µM

NSC122390 - 14 µM

From this analysis, a general structure for NSC119910 analogs was identified and is represented as Formula III.

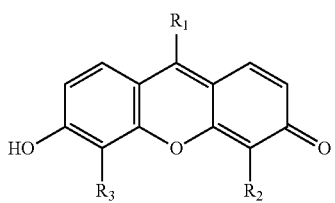

FORMULA III wherein, $R_1$ can be a substituted or unsubstituted alkyl, substituted or unsubstituted alkenyl, substituted or unsubstituted cycloalkyl, or substituted or unsubstituted cycloalkenyl; and $R_2$ and $R_3$ are independently hydrogen or a hydroxyl group. In particular embodiments, $R_2$ and $R_3$ are both hydroxyl.

As used herein, alkyl refers to a straight or branched hydrocarbon chain consisting solely of carbon and hydrogen atoms, containing no saturation, having from one to eight carbon atoms.

Alkenyl is intended to mean an aliphatic hydrocarbon group containing at least one carbon-carbon double bond and which may be a straight or branched chain having from 2 to about 10 carbon atoms.

Cycloalkyl denotes a non-aromatic mono or multicyclic ring system of about 3 to 12 carbon atoms.

As used herein, the term cycloalkenyl refers to a mono or multicyclic ring system containing in the range of about 3 to 12 carbon atoms with at least one carbon-carbon double bond.

Substituents in the substituted alkyl, cycloalkyl, alkenyl or cycloalkenyl groups include, but are not limited to, hydroxy, carboxyl, halogen (e.g., fluorine, chlorine, bromine, or iodine), or substituted or unsubstituted alkyl. With the exception of NSC157411 and NSC122390, analogs of NSC119910 generally contained hydroxyl groups in the $R_2$ and $R_3$ positions of Formula III, which appeared to facilitate binding; and a carboxyl-substituted alkyl, cycloalkyl, alkenyl or cycloalkenyl substituent at $R_1$ of Formula III, which appeared to modulate activity, but was not required for binding.

Accordingly, a further embodiment of the present invention is a compound having a structure of Formula III and pharmaceutically acceptable salts and complexes thereof.

Figure 6:
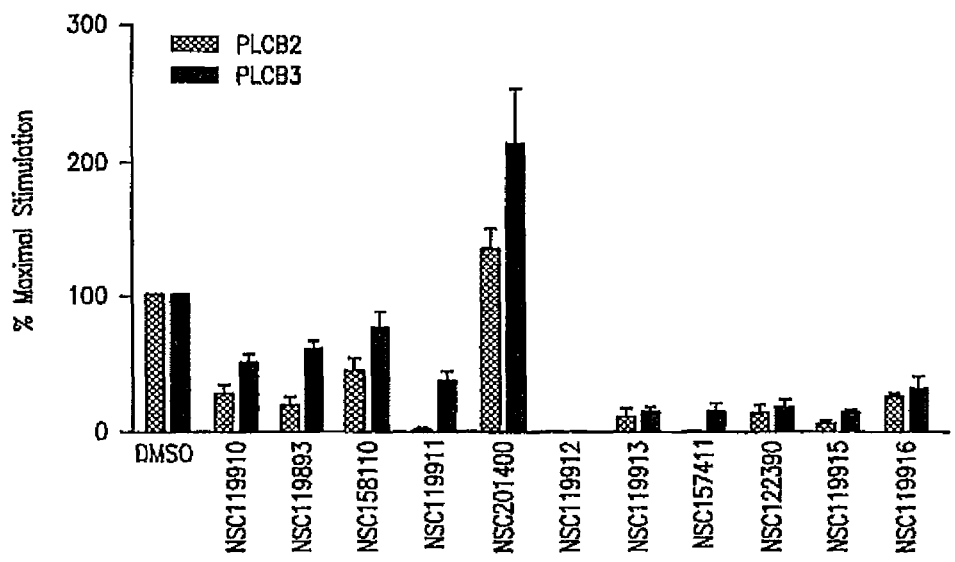
FIG. 6 is a bar graph illustrating inhibition of PLC-β2 and PLC-β3 activation in the presence of exemplary compounds of the instant invention.

The ability of NSC119910 analogs to selectively modulate activation PLC-β2 and -β3 was analyzed. In this assay, PLC-β2 and PLC-β3 were purified and PLC enzymatic activity was measured in the presence or absence of purified βγ and in the presence or absence of analog. The results of this analysis indicated that NSC119911 appeared to block PLC-β2 activation more effectively than PLC-β3 activation and NSC201400 selectively potentiated PLC-β3 activation despite blocking peptide binding to βγ (FIG. 6). Further, while NSC119910, NSC and analog NSC119893 block $Ca^{2+}$ mobilization, they do so without interfering with fMLP-dependent ERK activation. Likewise, NSC119911, NSC158110, and NSC201400 also do not interfere with fMLP-dependent ERK activation.

The compounds disclosed herein as well as those found to bind to the protein interaction site of Gβ and interfere with protein interactions at this surface can be used in a method for modulating (i.e., blocking or inhibiting, or enhancing or potentiating) at least one activity of a G protein. Such a method involves contacting a G protein either in vitro or in vivo with an effective amount of an agent that interacts with at least one amino acid residue of the protein interaction site of the G protein β subunit so that at least one activity of the G protein is modulated. An effective amount of an agent is an amount which reduces or increases the activity of the G protein by 10%, 20%, 30%, 40%, 50%, 60%, 70%, 80%, 90% or 100%. Such activity can be monitored based on protein-protein interactions or enzymatic assays detecting activity of downstream proteins.

As will be appreciated by one of skill in the art, modulating one or more G protein activities can be useful in selectively analyzing G protein signaling events in model systems as well as in preventing or treating diseases and disorders involving G protein βγ subunit signaling. The selection of the compound for use in preventing or treating a particular disease or disorder will be dependent upon the particular G protein-dependent downstream protein involved in the disease or disorder. For example, a compound which interacts with Lys57, Trp99, Met101, Leu117, Asp186, Asp228, Asp246 and/or Trp332 of Gβ would be useful in preventing or treating adenylyl cyclase-associated diseases or disorders, whereas a compound which interacts with Lys57, Tyr59, Trp99, Met101, Leu117, Tyr146, Met188, Asp246, and/or Trp332 may be more suitable for GRK2-associated diseases or disorders. It is contemplated that this selectivity for specific downstream proteins may reduce side effects associated with antagonists which inhibit all activities associated the G protein βγ subunit signaling.

Prevention or treatment typically involves the steps of first identifying a patient at risk of having or having a disease or disorder involving at least one G protein βγ subunit activity (e.g., congestive heart failure, addiction, hyper- or hypo-inflammation, or opioid tolerance). Once such an individual is identified using, for example, standard clinical practices, said individual is administered a pharmaceutical composition containing an effective of a selective compound disclosed herein or identified in the screening methods of the invention. In most cases this will be a human being, but treatment of agricultural animals, e.g., livestock and poultry, and companion animals, e.g., dogs, cats and horses, is expressly covered herein. The selection of the dosage or effective amount of a compound is that which has the desired outcome of reducing or reversing at least one sign or symptom of a disease or disorder involving G protein βγ subunit signaling in a patient. For example, some of the general signs or symptoms associated with congestive heart failure include increased heart rate, increased respiratory rate, breathing faster and deeper than normal, breathlessness, irritability, restlessness, an unexplained fussiness, swelling, puffiness, edema, sudden weight gain or poor weight gain, decrease in appetite, diaphoresis, cough, congestion or wheezing, a decrease in activity level, fatigue, listlessness, decrease in urine output, or pale, mottled or grayish appearance in skin color. General signs or symptoms associated with addiction include, but are not limited to, changes in attitude, appearance, and relationships with others, whether at home, school or work and other behavioral changes.

When preventing or treating an inflammatory condition, the selective modulation of either the PLC pathway or PI3Kγ will be useful in treating different inflammatory conditions. For example, to reduce neutrophil migration into sites of inflammation (e.g., in arthritis) it is desirable to administer a compound which selectively inhibits the activation of PI3Kγ thereby reducing the injury to tissues that contribute to the pathophysiology of the inflammatory diseases. Conversely, to facilitate an inflammatory response, e.g., to enhance immune responses to bacterial or viral infection, it is desirable to administer a compound which selectively inhibits the activation of the PLC pathway.

Pharmaceutical compositions can be in the form of pharmaceutically acceptable salts and complexes and can be provided in a pharmaceutically acceptable carrier and at an appropriate dose. Such pharmaceutical compositions can be prepared by methods and contain carriers which are well known in the art. A generally recognized compendium of such methods and ingredients is Remington: The Science and Practice of Pharmacy, Alfonso R. Gennaro, editor, 20th ed. Lippincott Williams & Wilkins: Philadelphia, Pa., 2000. A pharmaceutically-acceptable carrier, composition or vehicle, such as a liquid or solid filler, diluent, excipient, or solvent encapsulating material, is involved in carrying or transporting the subject compound from one organ, or portion of the body, to another organ, or portion of the body. Each carrier must be acceptable in the sense of being compatible with the other ingredients of the formulation and not injurious to the patient.

Examples of materials which can serve as pharmaceutically acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Wetting agents, emulsifiers and lubricants, such as sodium lauryl sulfate and magnesium stearate, as well as coloring agents, release agents, coating agents, sweetening, flavoring and perfuming agents, preservatives and anti-oxidants can also be present in the compositions.

The compositions of the present invention can be administered parenterally (for example, by intravenous, intraperitoneal, subcutaneous or intramuscular injection), topically (including buccal and sublingual), orally, intranasally, intravaginally, or rectally according to standard medical practices.

The selected dosage level will depend upon a variety of factors including the activity of the particular compound of the present invention employed, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of a compound at levels lower than that required in order to achieve the desired therapeutic effect and gradually increase the dosage until the desired effect is achieved. This is considered to be within the skill of the artisan and one can review the existing literature on a specific compound or similar compounds to determine optimal dosing.

As will be understood by those of skill in the art upon reading this disclosure, additional compounds to those exemplified herein can be identified routinely in accordance with the screening methods taught herein. Additional compounds for screening can be selected randomly by one skilled in the art, based upon computational prediction, and/or based upon their containing a structure of Formula I, II or III or a structure similar to that of the exemplary compounds disclosed herein.

The invention is described in greater detail by the following non-limiting examples.

Example 1

Materials

Peptides were purchased from Alpha Diagnostic International (San Antonio, Tex.) or SIGMA®-Genosys (St. Louis, Mo.), HPLC purified to greater than 90% and masses confirmed by mass spectroscopy. Ni-NTA agarose was from QIAGEN® (Valencia, Calif.). Streptavidin-coated poly-styrene beads were from Spherotec (Libertyville, Ill.). HRP-conjugated anti-M13 antibody was from Amersham Biosciences (Piscataway, N.J.). HRP-conjugated Neutravidin was from Pierce (Rockford, Ill.). All molecular biology reagents were from INVITROGEN™ (Carlsbad, Calif.) unless otherwise indicated.

Example 2

Expression and Purification of $G\beta_1\gamma_2$ and SIGK Peptide

Baculoviruses harboring cDNA for wild-type bovine $G\beta_1$ and N-terminally $(His)_6$-tagged bovine $G\gamma_2$ were used to produce proteins of the same. High 5 cells (INVITROGEN™, Carlsbad, Calif.; 2×10⁶ cells/mL) were infected with high titer Gβ₁ and Gγ₂ baculoviruses. Gβ₁γ₂ was purified according to standard methods (Kozaza and Gilman (1995) *J. Biol. Chem.* 270:1734-41), with modifications. All steps were carried out at 4° C. Cells were harvested 60 hours post-infection by centrifugation at 2600 g, then resuspended in 50 mL of lysis buffer (20 mM HEPES, pH 8, 150 mM NaCl, 5 mM β-ME, 1 mM EDTA, 1 mL SIGMA® protease inhibitor cocktail P-2714) per liter of cell culture. Cells were lysed by sonication and centrifuged at 2600 g to pellet the membranes. Resuspension and homogenization of membranes was accomplished by douncing in 100 mL lysis buffer. The membranes were solubilized by adding 1% Lubrol (C12E10, SIGMA®, St. Louis, Mo.) with stirring and the resultant solution clarified by ultracentrifugation at 125,000 g. The supernatant was loaded onto Ni-NTA agarose (QIAGEN®, Valencia, Calif.) equilibrated with lysis buffer 4-1% Lubrol. The column was washed and the Lubrol exchanged for sodium cholate using buffers Ni-A (20 mM HEPES, pH 8, 0.4 M NaCl, 5 mM β-ME, 0.5% Lubrol, 0.15% cholate) and Ni—B (20 mM HEPES pH 8, 0.1 M NaCl, 5 mM β-ME, 0.25% Lubrol, 0.3% etiolate). Gβ1γ2 eluted in Ni—C (20 mM HEPES pH 8, 0.01 M NaCl, 5 mM β-ME, 1% cholate, 200 mM imidazole). The eluate was loaded onto a HITRAP™ Q (Amersham Biosciences, Piscataway, N.J.) column pre-equilibrated with QA (20 mM HEPES, pH 8, 5 mM β-ME, 0.7% CHAPS, 1 mM EDTA). Gβ₁γ₂ eluted in a gradient using QB (QA 1.0 M NaCl). Fractions containing Gβ₁γ₂ were analyzed by SDS-PAGE and pooled. Gel filtration was performed using a tandem SEPHADEX® 75:SEPHADEX® 200 column (Amersham Biosciences, Piscataway, N.J.) equilibrated with buffer GF+CHAPS (20 mM HEPES, pH 8, 150 mM NaCl, 10 mM β-ME, 1 mM EDTA, 0.7% CHAPS). The purified yield was typically 1 mg Gβ₁γ₂ per liter of cell culture.

SIGK peptide (Ser-Ile-Gly-Lys-Ala-Phe-Lys-Ile-Leu-Gly-Tyr-Pro-Asp-Tyr-Asp; SEQ ID NO:2) was synthesized using well-established methods. No modifications were made to the peptide termini; purification was by reverse phase-HPLC chromatography on a VYDAC® C4 semi-preparative column.

Example 3

Crystallography

SIGK peptide was added to Gβ₁γ₂ in 1.5 molar excess, and the Gβ₁γ₂•SIGK complex was used at 7 mg/mL for crystallization. Crystals were grown by vapor diffusion using equal volumes (2 μL) of protein and reservoir solution (15-17% PEG 4000, 100 mM HEPES, pH 7.5, 0.01-0.05 M Na-Acetate, 10% glycerol) at 20° C. Crystals attained dimensions of 150 μm×50 μm×20 μm within one week. Crystals were cryo-protected in 15% glycerol and frozen in liquid nitrogen.

Native crystals of Gβ₁γ₂•SIGK were screened at Advanced Light Source (ALS) beamlines 8.2.1 and 8.2.2 (Berkeley, Calif.) and at the Advanced Photon Source (APS) beamline BM-19 (Chicago, Ill.). A dataset from ALS 8.2.2 was used to determine the structure. Over 100 crystals were screened; diffraction limits varied from 7 Å to the 2.7 Å dataset used for structure determination. Diffraction data were indexed, integrated, and scaled using the software package HKL2000 (Otwinowski and Minor (1997) In: *Methods in Enzymology*, Vol. 276:307-326) (Table 4). The space-group of the crystals was $P2_12_12_1$.

TABLE 4

| Data Collection | |
|---|---|
| Space Group | $P2_12_12_1$ |
| Unit Cell | |
| a (Å) | 45.468 |
| b | 74.669 |
| c | 108.023 |
| α (°) | 90 |
| β | 90 |
| γ | 90 |
| $D_{min}$ (Å) | 2.7 |
| Unique Reflections | 9729 |
| Redundancy[1] | 3.5 (1.8) |
| Completeness (%)[1] | 90.1 (56.2) |
| $<I/\sigma>$[1] | 13.5 (1.6) |
| Rsym[1,2] | 8.7 (41.4) |
| Mosaicity (°) | 2.3 |
| Wilson B-factor (Å) | 61.8 |
| Refinement | |
| Resolution (Å) | 45.4-2.7 |
| Number of atoms[3] | |
| Protein | |
| Water | |
| $R_{work}$ (%)[4] | |
| $R_{free}$ (%)[5] | |
| R.m.s Deviations | |
| Bond lengths (Å) | 0.006 |
| Bond Angles (°) | 1.3 |
| R.m.s. B factors (Å²) | |
| Bonded main chain | 1.29 |
| Bonded side chain | 18.1 |
| Average B-factor (Å)[6] | 46.3 |

The final model contains residues 2-340 of Gβ₁ (of 340), 7-52 of Gγ₂ (of 68), 1-13 of SIGK (of 15), and 37 water molecules.
[1]Numbers in parentheses correspond to the highest resolution shell, 2.8-2.7 Å.
[2]$R_{sym} = \Sigma_h \Sigma_i |I_i(h) - <I(h)>|/\Sigma_h \Sigma_i I_i(h)$, where $I_i(h)$ and $<I(h)>$ are the $i^{th}$ and mean measurement of the intensity of reflection h, respectively.
[3]The final model contains residues 2-340 of Gβ₁ (of 340), 7-52 of Gγ₂ (of 68), and 1-13 of SIGK (of 15).
[4]$R_{work} = \Sigma_h ||F_o(h)| - |F_c(h)||/\Sigma_h |F_o(h)|$, where $F_o(h)$ and $F_c(h)$ are the observed and calculated structure factors, respectively. An I/σ cutoff was not used in the final calculations of R-factors.
[5]$R_{free}$ is the R-factor obtained for a test set of reflections consisting of a randomly selected 8% of the data.
[6]B-factors at the N-termini, including Gβ₁ residues 2-41 and Gγ₂ residues 7-13, are greater than 80 Å².

The structure of the Gβ₁γ₂•SIGK complex was solved by the molecular replacement method using the program PHASER (Storoni, et al. (2004) *Acta Crystallogr. D Biol. Crystallogr.* 60:432-8; Read (2001) *Acta Cxystallogr. D Biol. Crystallogr.* 57:1373-82). The coordinates of Gβ₁γ₂ in the Gβ₁γ₂•GRK2 complex (10 MW, 100% sequence identity) were used as the search model. After rigid body refinement using the maximum likelihood minimization target in CNS version 1.1 (Adams, et al. (1997) *Proc. Natl. Acad. Sci. USA* 94:5018-23; Brunger, et al. (1998) *Acta Crystallographica Section D* 54:905-921), the model was further refined by using a combination of simulated annealing, Powell minimization, and B factor refinement. The sigma A-weighted 2Fo-Fc electron density map computed with refined phases revealed clear main chain density for ten residues of the SIGK peptide along with identifiable side chain density for several SIGK residues. Subsequent model building was performed in O (Jones, et al. (1991) *Acta Crystallographica Section A* 47:110-119) followed by simulated annealing, energy minimization, and B factor refinement using CNS. PROCHECK (Laskowski, et al. (1993) *J. Appl. Crystallography* 26:283-291) analysis indicates that all residues exhibit main chain conformations in most favored or additional allowed regions of ϕ, ψ space (Table 4). Calculations of surface accessibility, Gβ1γ2•SIGK contacts and RMSD between structures were carried out using programs in the CNS suite.

Example 4

Construction and Partial Purification Biotinylated $G\beta_1\gamma_2$ (b-βγ) and b-βγ Mutants Wild-type $G\beta_1$ and $G\beta_1$ mutants were made in the baculovirus vector PDW464 which encodes a biotinylation site at a lysine upstream of the amino terminus of $G\beta_1$ (Goubaeva, et al. (2003) supra). Mutants were generated by overlap extension PCR using standard protocols. The wild-type and mutant $G\beta_1$ constructs consisted of a 20 amino acid biotin acceptor peptide (BAP) sequence fused in-frame with the amino-terminus of rat $G\beta_1$ subunit. When coexpressed with biotin holoenzyme synthetase (BirA) in Sf9 cells, the $G\beta_1$ subunit becomes covalently biotinylated in vivo at the Specific lysine acceptor residue in the BAP. Using this approach, 1-2 mg protein of purified protein can be obtained per liter of Sf9 insect cells. As 45 ng of protein is used in the phage ELISA assay, a single purification is sufficient for 10,000 to 30,000 binding assays.

Baculoviruses were generated via the BAC-TO-BAC® system following the manufacturer's instructions (GIBCO/BRL, Gaithersburg, Md.). Sf9 cells (200 mL) were triply infected with 0.5 mL baculovirus encoding $(His)_6$-$G\alpha_{i1}$, 4 ml of $G\gamma_2$ virus, and 4 mL of either wild-type or mutated $G\beta_1$ virus. $G\beta_1\gamma_2$ dimers were purified 60 hours post-infection using a well-established method with modifications as indicated (Kozasa and Gilman (1995) supra). Cell pellets were lysed in 4 mL lysis buffer (50 mM HEPES, pH 8.0, 3 mM $MgCl_2$, 10 mM β-mercaptoethanol, 1 mM EDTA, 100 mM NaCl, 10 μM GDP, and protease inhibitors) by four freeze-thaw cycles in liquid nitrogen. Membranes were solubilized using 1% sodium cholate, clarified by ultracentrifugation at 100,000 g for 20 minutes, diluted into buffer containing 0.5% lubrol, and mixed with Ni-NTA resin. After washing thoroughly, $G\beta_1\gamma_2$ subunits were eluted from bound $G\alpha_{i1}$ by mixing beads with buffer containing 50 mM $MgCl_2$, 10 mM NaF, 10 μM $AlCl_2$, 1% cholate, and 5 mM imidazole at room temperature for one hour. The concentrations of b-βγ and b-βγ mutants were analyzed by comparative immunoblotting and chemiluminescence. Proteins were separated by SDS-PAGE, transferred to nitrocellulose, and probed with HRP-neutravidin (Pierce, Rockford, Ill.). The chemiluminescent signal was measured using an EPI-CHEM II™ darkroom system (UVP Bioimaging Systems, Upland, Calif.). Concentrations of eluted b-βγ dimers were determined by comparing to a standard curve of fully purified 100% biotinylated $G\beta_1\gamma_2$ from at least two separate gels.

Example 5 b-βγ Binding Assay

Phage ELISA assays used to assess peptide binding to wild-type and mutant b-βγ were performed according to standard methods (Smrcka and Scott (2002) Methods Enzymol. 344:557-76). Briefly, 1 μg streptavidin was immobilized in the well of a 96-six well plate overnight at 4° C. The wells were blocked with 100 μL of 2% bovine serum albumin (BSA) in Tris-buffered saline (TBS) for 1 hour at 4° C. followed by three washes of 1×TBS/0.5% TWEEN®. Forty μL of 25 nM $bG\beta_1\gamma_2$ in TBS/0.5% TWEEN® was added to each well and incubated at 4° C. for 1.5 hour. The wells were washed, followed by the addition of $1\times10^6$ to $1\times10^{10}$ phage particles and incubated at 4° C. for 3 hours. The wells were then washed six times with TBS/0.5% TWEEN® followed by addition of 40 μL of 1:5000 dilution of anti-M13 antibody (Pharmacia, Uppsala, Sweden) and incubated at room temperature for 1 hour. The wells were washed, followed by the addition of 40 μL of (2,2'-Azino-bis(3-ethylbenzthiazoline)-6-sulfonic acid (ABTS) and the colorimetric reaction was monitored at 405 nm. Non-specific binding was subtracted for each reading.

Signals obtained with partially purified b-βγ subunits were similar to signals obtained from fully purified b-βγ subunits. Blocking of $G\alpha_i$•$G\beta_1\gamma_2$ binding was assessed by simultaneously adding 200 pM FITC-$G\alpha_i$ with or without SICK to 50 pM immobilized b-βγ and measuring the amount of FITC-$G\alpha_i$ bound to the beads by flow cytometry according to standard methods (Ghosh, et al. (2003) supra; Sarvazyan, et al. (1998) J. Biol. Chem. 273:7934-40).

Example 6

Architecture of the $G\beta_1\gamma_2$•SIGK Complex

Unless indicated otherwise, amino acid residues having the prefix "s" are indicative of SICK residues.

$G\beta_1$ is a β-propeller composed of seven four-stranded β-sheets ("blades") and an N-terminal extended helix that interacts extensively with $G\gamma_2$. Each sheet is composed of WD-40 repeats connected by loops of variable length. Residues 2-340 of $G\beta_1$ are included in the model. B factors throughout the core of $G\beta_1$ are less than 40 Å$^2$. Residues with B factors >60 Å$^2$ are found in three loop regions: Lys127-Ser136 in blade two, Arg214-Met217 in blade four, and Ser265-Ile269 in the loop connecting blades six and seven. $G\gamma_2$ forms a helix with a kink made by residues Asn24-Lys29 and a coil region beginning at residue His44. The average B factor within the $G\gamma_2$ molecule is 44 Å$^2$. No electron density was observed for the N-terminal seven residues and the C-terminal sixteen residues of $G\gamma_2$ or the prenyl lipid modification at the C-terminus of $G\gamma_2$.

SIGK forms an α-helical structure broken by a glycine at position 10. The C-terminal three residues form an extended structure that stretches away from the $G\beta_1$ molecule and is supported by crystal contacts between sPro12 and sAsp13 with Thr47 and Lys337 from a symmetry-related $G\beta_1$ molecule. The B factors for the N- (SSer1, sIle2) and C-terminal (sGly10-sAsp13) residues of SIGK are greater than 50 Å$^2$; those for all other residues are between 30-50 Å$^2$. The electron density for the main chain atoms in residues 1-13 is well-defined; three of the SICK side chains that do not contact $G\beta_1$ (sIle2, sLys7, and sAsp13) are disordered. The peptide binds across the "top" face of $G\beta_1$ and is buried 970 Å$^2$ total solvent-accessible surface area. The peptide makes no contact with the $G\gamma_2$ subunit, which is bound to the "bottom" surface of the $G\beta_1$ torus.

The SICK contact surface on $G\beta_1$ was separated into two regions: an acidic region on $G\beta_1$ that interacts with the N-terminus of the peptide, and a largely nonpolar region that interacts with the C-terminus of the peptide. In total, thirteen $G\beta_1$ residues directly contact SIGK, contributed by six of the seven blades of the β-propeller (Table 5).

TABLE 5

| $G\beta_1$-Interacting Residues | | SIGK-Interacting Residues | | Distance (Å) | Type of Interaction |
|---|---|---|---|---|---|
| Lys57 | Cε | Leu9 | O | 3.35 | Nonpolar |
|  | Cε | Gly10 | Cα | 3.99 | Nonpolar |

TABLE 5-continued

| Gβ$_1$-Interacting Residues | | SIGK-Interacting Residues | | Distance (Å) | Type of Interaction |
|---|---|---|---|---|---|
| Tyr59 | OH | Leu9 | O | 2.66 | Polar |
|  | Cε | Ile8 | O | 3.87 | Nonpolar |
| Trp99 | Nε1 | Tyr11 | OH | 2.81 | Polar |
|  | Cδ1 | Leu9 | Cδ2 | 3.59 | Nonpolar |
| Val100 | O | Leu9 | Cδ2 | 3.75 | Nonpolar |
| Met101 | Cε | Ile8 | Cγ2 | 3.46 | Nonpolar |
|  | Cε | Ala5 | O | 3.52 | Nonpolar |
|  | Cε | Leu9 | Cδ2 | 3.54 | Nonpolar |
| Leu117 | Cδ1 | Ile2 | Cγ2 | 3.46 | Nonpolar |
|  | Cδ2 | Ala5 | Cβ | 3.68 | Nonpolar |
|  | Cδ2 | Leu9 | Cδ1 | 3.80 | Nonpolar |
| Tyr145 | Cε2 | Ser1 | O | 3.19 | Nonpolar |
|  | OH | Lys4 | Cγ | 3.45 | Nonpolar |
|  | Cδ2 | Ala5 | Cβ | 3.81 | Nonpolar |
| Asp186 | Oδ2 | Ser1 | O | 3.03 | Polar |
| Met188 | Cε | Ile8 | Cδ1 | 3.31 | Nonpolar |
|  | Cε | Lys4 | Cε | 3.48 | Nonpolar |
| Asp228 | Oδ2 | Lys4 | Nζ | 3.23 | Polar |
| Asn230 | Nδ2 | Lys4 | Nζ | 2.82 | Polar |
| Asp246 | Oδ2 | Lys4 | Nζ | 3.05 | Polar |
| Trp332 | Cζ2 | Ile8 | O | 3.12 | Nonpolar |
|  | CH2 | Gly10 | Cα | 3.57 | Nonpolar |

The N-terminal binding surface is centered on an electrostatic interaction in which sLys4 projects into a negatively charged binding pocket on Gβ$_1$γ$_2$ where it forms hydrogen-bonded or charge interactions with Asp228, Asn230, and Asp246. A hydrogen bond between the carbonyl oxygen of Asp228 and the main chain nitrogen of Asp246 stabilizes the three acidic residues on Gβ$_1$. Met188 participates in van der Waals interactions with the alkyl chain of sLys4, and Asp186 forms a polar contact with the carbonyl oxygen of sSer1 and also makes a hydrogen bond to the amide of Cys204. Additionally, Tyr145 forms van der Waals interactions with the main chain oxygen of sSer1, the sLys4 side chain, and the Cβ atom of sAla5, and forms a hydrogen bond with the nearby amide of Gly162. The side chain of Leu117 is within van der Waals contact distances of the side chains of sIle2 and sAla5. Together, these nine Gβ$_1$ residues form a surface that tethers SIGK to Gβ$_1$ using charged and nonpolar interactions.

Mutational analysis of SIRK and SIGK peptides can now be interpreted in the context of the SIGK•Gβ$_1$γ$_2$ structure (Scott, et al. (2001) supra; Goubaeva, et al. (2003) supra). Wild-type SIRK peptide inhibits the activation of PLC β2 by Gβ$_1$γ$_2$ with an IC$_{50}$ of 5 μM. Substitution of sLys4 with alanine in the SIRK peptide lowers the IC$_{50}$ of the peptide 12-fold, and mutation of sAla5 to glycine lowers the IC$_{50}$ by 13-fold. Mutation of sIle2 to alanine reduces IC$_{50}$ of the peptide by 4-fold, and mutation of sSer1 to alanine has no effect on IC$_{50}$ (Scott, et al. (2001) supra). The SIGK•Gβ$_1$γ$_2$ structure indicates that the main chain of sSer1 and the side chains of sIle2, sLys4, and sAla5 contact multiple resides on Gβ, thereby explaining this mutational data.

To measure the contribution of the Gβ$_1$ residues observed at the Gβ$_1$γ$_2$•SIGK interface to the binding energy for the complex, two approaches were utilized. First, an ELISA assay was used to measure binding of immobilized Gβ$_1$γ$_2$ subunits to phage displaying the SIGK sequence (Table 6). The ELISA binding data were then correlated with IC$_{50}$ values for SIGK as a competitor of Gβ$_1$γ$_2$ association with Gα$_{i1}$ (Table 7). Both assays were then carried out with Gβ$_1$γ$_2$ heterodimers containing mutations in the Gβ$_1$ subunit. In the N-terminal binding surface, mutation of Gβ$_1$ Asn230 to alanine decreased the affinity of Gβ$_1$γ$_2$ for peptide 10-fold (Table 6). Single mutation of Gβ$_1$ residues Asp186, Met188, Tyr145, and Leu117 to alanine also resulted in Gβ$_1$γ$_2$ dimers with drastically decreased affinity for SIGK (Table 6). Gβ$_1$ mutants in which either Asp228 or Asp246 were substituted with alanine did not dimerize with Gγ$_2$ and therefore were not analyzed. However, a mutant in which Asp228 was substituted with serine caused only a slight loss in binding affinity for SIGK peptide (Table 6). Thus, many of the Gβ$_1$ residues that create the N-terminal SIGK binding interface contribute strongly to the energy of binding.

TABLE 6

| Gβ$_1$γ$_2$ Mutation | % of Wild-Type Signal (mean ± SD) |
|---|---|
| Lys57Ala | 18.6 ± 4.6 |
| Tyr59Ala | 24.7 ± 15.2 |
| His62Ala | 111.2 ± 11.3 |
| Trp99Ala | 66.0 ± 7.7 |
| Met101Ala | 32.2 ± 15.5 |
| Leu117Ala | 2.1 ± 2.4 |
| Tyr145Ala | 0.8 ± 0.9 |
| Asp186Ala | 13.0 ± 13.1 |
| Met188Ala | 2.5 ± 3.7 |
| Asn230Ala | 22.4 ± 4.2 |
| Asp246Ser | 66.5 ± 7.5 |
| Phe292Ala | 109.1 ± 21.4 |
| His311Ala | 94.3 ± 18.9 |
| Arg314Ala | 50.2 ± 5.0 |
| Trp332Ala | 7.1 ± 3.7 |

Amino acids that contact the SIGK peptide were individually mutated to alanine (or serine for Asp246) and binding to peptide was assayed using a phage ELISA. Immobilized b-βγ was incubated with phage displaying SIGK peptide. Phage binding was detected using an α-phage antibody; the raw data was absorbance at 405 nm. Data shown are the mean ± SD of triplicate determinations from three independent experiments.

TABLE 7

| | % Maximal Fα Binding (± SD) | | | |
|---|---|---|---|---|
| Log [SIGK] M | Wild-Type | Met188Ala | Trp332Ala | Arg314Ala |
| −7 | 100.0 ± 0.0 | 100.0 ± 0.0 | 100.0 ± 0.0 | 100.0 ± 0.0 |
| −5.7 | 55.0 ± 10.8 | 101.3 ± 7.6 | 72.7 ± 2.3 | 65.3 ± 5.8 |
| −5 | 45.7 ± 16.3 | 80.7 ± 7.6 | 57.3 ± 7.2 | 47.0 ± 11.1 |
| −4.7 | 17.3 ± 3.8 | 72.7 ± 11.2 | 33.0 ± 3.5 | 30.7 ± 4.2 |
| −4.4 | 13.3 ± 1.5 | 40.0 ± 7.1 | 24.7 ± 3.5 | 21.0 ± 0.0 |
| −4.1 | 5.8 ± 4.8 | 33.0 ± 7.2 | 16.7 ± 1.2 | 13.0 ± 3.0 |

SIGK competition for FITC-Gα$_{i1}$β$_1$γ$_2$ interactions with representative Gβ$_1$ subunit mutants. SIGK and FITC-α$_{i1}$ were simultaneously added to streptavidin beads coated with wild-type or mutant b-βγ protein and the amount of FITC-α$_{i1}$ bound to the beads was assayed by flow cytometry. Data are shown as the mean of triplicate determinants +/− standard deviation of a representative experiment. The experiment was repeated two (Met188A) or three (wild-type, Arg314A, Trp332A) times with similar results. Comparison of the two assays over a selection of mutants that spanned the range of SIGK binding affinities indicates that a 50% loss of binding translates into a five-fold increase in IC$_{50}$, a 75% loss of binding corresponds to a 10-fold increase, a 90% loss is a 20-fold shift and a 98% loss is a 50-fold shift. The IC$_{50}$ values are as follows: wild-type = 0.47 μM, Arg314A = 1.5 μM, Trp332A = 9 μM, and Met188A = 22 μM.

The second area of binding involves most of the C-terminal residues of SIGK (sAla5-sGly11), which pack against a largely hydrophobic pocket on Gβ$_1$. This pocket extends 11 Å from Trp332 on blade seven to Met188 in blade two. Eight Gβ$_1$ residues are in direct contact with the C-terminal surface of SIGK, and two more Gβ$_1$ residues support the residues directly involved in the SIGK interaction. Met188, which interacts with sLys4 in the N-terminal interface, is also within contact distance of the side chain of sLeu8. SICK residues sAla5, sLeu8 and sLeu9 are complimented by van der Waals interactions with Leu117, Met101, Trp99, Tyr59 and the alkyl chain of Lys57. The main chain oxygen of Val100 interacts with the side chain of sLeu9. The indole imine of Trp99 forms a hydrogen bond with the hydroxyl group of sTyr11 and the side chain of Trp332 makes contact with the main chain oxygen of sIle8 and the Cα of sGly10. The side chains of Lys57 and Arg314 are positioned on either side of Trp332 and support its orientation in the binding site. Arg314 also forms a hydrogen bond with Trp332, and Lys57 with the nitrogen of Gln75, further stabilizing this interaction surface on G$\beta_1$. Data from alanine scanning of the peptide (Scott, et al. (2001) supra; Goubaeva, et al. (2003) supra) validate these structural observations. Mutation of sIle8, sLeu9 or sGly10 to alanine increases the IC$_{50}$ for inhibition of PLC activation by 40-fold (5 μM to 200 μM), 60-fold and 12-fold, respectively (Scott, et al. (2001) supra). The same mutation of sLeu9 also blocks the ability of SIRK to enhance ERK1/2 phosphorylation in RASM cells (Goubaeva, et al. (2003) supra).

Mutation of amino acids in G$\beta_1$ that constitute the SICK C-terminal binding surface caused a loss in affinity for the SICK peptide, although to different extents. Mutation of Leu117, Met188, or Trp332 to alanine nearly abrogated SIRK binding; mutants of Lys57, Tyr59, Met101, and Arg314 had more modest effects (Table 6 and Table 8). The Trp99 mutation resulted in a 4-fold decrease in affinity. A summary of all the G$\beta_1$ mutations (i.e., conversions to alanine) presented herein and their effects on SICK binding affinity is listed in Table 8.

TABLE 8

| | Loss in Affinity for SIGK Peptide | | | | |
|---|---|---|---|---|---|
| | 75-100% | 50-75% | 25-50% | 0-25% | No Effect |
| G$\beta_1$ Residue | Lys57 Tyr59 Leu117 Tyr145 Asp186 Met188 Asn230 Trp332 | Met101 Arg314 | Trp99 Asn246 | His311 | His62 Phe292 |

Considering all of the data for the N-terminal and C-terminal SIGK binding interfaces, seven of the fifteen residues of the SIGK peptide and ten of the twelve G$\beta$ residues tested contribute significant binding energy to the interface, in good correlation with the structural model.

The binding surface of G$\beta_1$ in the G$\beta_1\gamma_2$•SIGK complex is not significantly changed upon SIGK binding. The RMSD between the core residues of G$\beta_1$ in the G$\beta_1\gamma_2$•SIGK complex and that in the uncomplexed G$\beta_1\gamma_1$ heterodimer (1TBG (Sondek, et al. (1996) Nature 379:369-74); Val40-Asn340, C$\alpha$ only) is 0.88 Å. However, the side chains of Trp99, Tyr59, Asp228, Leu117 and Met101 rotate to accommodate SIGK such that atoms within these residues undergo maximum displacements of 4.0 Å, 3.6 Å, 2.9 Å, 2.8 Å and 2.3 Å, respectively, relative to their positions in uncomplexed G$\beta_1$. The B factors for residues in the SIGK binding surface are close to the overall average for the complex. However, the B factor for Trp99 is reduced two-fold upon binding to SIGK, as indicated by comparison of normalized B factors of the respective structures. In this analysis, there are no large conformational changes or disorder to order transitions in G$\beta$ upon SIGK binding. The SIGK•G$\beta_1\gamma_2$ complex may be compared to those of five G$\beta_1\gamma_2$ complexes with protein targets: the G$\beta_1\gamma_2$•G$\alpha_{i1}$ heterotrimer (1GG2) (Wall, et al. (1995) supra; Wall, et al. (1998) supra) and the G$\beta_1\gamma_1$•G$\alpha_{t/i}$ heterotrimer (1GOT) (Lambright, et al. (1996) supra), the G$\beta_1\gamma_1$•phosducin complex (1AOR and 2TRC) (Loew, et al. (1998) supra; Gaudet, et al. (1996) supra), and the G$\beta_1\gamma_2$•GRK2 complex (10MW) (Lodowski, et al. (2003) supra). Superposition of the G$\beta_1\gamma_2$•SIGK complex with each of these structures yields average RMS deviations for G$\beta_1$ residues 40-340 of less than 1.0 Å (C$\alpha$ only). With the exception of a few residues involved in the G$\beta_1\gamma_2$•phosducin complex, the G$\beta\gamma$ heterodimer does not undergo significant structural rearrangement in order to bind protein targets, nor does it in the G$\beta_1\gamma_2$•SIGK structure.

Example 7

Measurement of α-βγ Interactions via Flow Cytometry

Fluorescein-labeled G$\alpha_{i1}$ (F$\alpha_{i1}$) was prepared in accordance with standard methods (Sarvazyan, et al. (1998) supra). Assays were used to determine peptide effects on G$\alpha$-G$\beta\gamma$ interactions included competition and dissociation assays (Ghosh, et al. (2003) supra). Briefly, for competition-based assays, 100 pM F$\alpha_{i1}$ and indicated concentrations of peptides were added to 50 pM b-G$\beta_1\gamma_2$ immobilized on $10^5$ beads per mL and incubated at room temperature for 30 minutes to reach equilibrium. The bead-associated fluorescence was then recorded in a BD Biosciences FACSCALIBUR™ flow cytometer. Data was corrected for background fluorescence and fit with a sigmoid dose response curve using Graph Pad Prism 4. To measure dissociation of F$\alpha_{i1}$ from b-G$\beta_1\gamma_2$, 100 pM of F$\alpha_{i1}$ was incubated with 50 pM immobilized b-G$\beta_1\gamma_2$ at room temperature for 15-20 minutes. The fluorescence of bound F$\alpha_{i1}$ subunit was measured, followed by the addition of a 200-fold excess of unlabeled G$\alpha_{i1}$ or peptides and the amount of F$\alpha_{i1}$ remaining bound to the beads was measured at the indicated times.

Example 8

Molecular Recognition at the Protein Interaction Site

Having demonstrated that the interface for SIGK peptide binding was divided into two broad interactions) a C-terminal binding interface, which contacts the hydrophobic core of the peptide (amino acids 8-10, Ile-Leu-Gly), and an N-terminal interface, which associates with the N-terminus (Lys4 primarily) of the peptide, the molecular basis for recognition of the peptide was determined. Accordingly, amino acids of the common binding surface of G$\beta_1$ were individually alanine substituted to determine which amino acids were most critical for the interaction of G$\beta_1\gamma_2$ with nine different SICK peptide derivatives (Table 9).

TABLE 9

| Phage Name | Sequence* | SEQ ID NO: | Group |
|---|---|---|---|
| 3.14 | SIGKALFILGYPDYD | 5 | I |
| 2F | LCSKAYLLLGQTC | 6 | |
| C1 | SCKRTKAQILLAPCT | 7 | |
| C14 | WCPPKAMTQLGIKAC | 8 | II |
| 3C | SCGHGLKVQSTIGACA | 9 | |
| C4 | SCEKRYGIEFCT | 10 | III |
| C5 | SCEKRLGVRSCT | 11 | |
| C8 | SCARFFGTPGCT | 12 | |
| C2 | WCPPKLEQWYDGCA | 13 | IV |

*Underlined residues denote the lysine residue contacting the N-terminus, and the hydrophobic core residues.

The nine peptides were selected to represent the different consensus groups of peptides previously identified (See Scott et al. (2001) supra; Table 9) and to compare binding characteristics within and between consensus groups. Binding of phage displaying these peptides to wild-type Gβ₁γ₂ gave ELISA signals that were different, but fell within a similar range (25 to 100% binding relative to phage 3.14). As disclosed herein, the binding signal obtained in the ELISA assay was correlated to a loss in affinity by comparing the results to behavior of the peptide in a solution based assay. For example, a mutant displaying an 80% loss of binding in an ELISA had a corresponding 10-fold shift in peptide affinity in solution. For the purposes of present disclosure, any substitution that decreased the binding to less than 20% of the wild-type binding was considered to be a critical binding contact for that peptide. Data obtained from this analysis is presented in Table 10.

Ser-Cys-Lys-Arg-Thr-Lys-Ala-Gln-Ile-Leu-Leu-Ala-Pro-Cys-Thr (C1; SEQ ID NO:7) absolutely requires Trp99 for binding. The reverse is true for Tyr145 where SIGK binding has an absolute requirement for Tyr145 and Ser-Cys-Lys-Arg-Thr-Lys-Ala-Gln-Ile-Leu-Leu-Ala-Pro-Cys-Thr (C1; SEQ ID NO:7) binding is not affected by this mutation.

The N-terminus of SIGK interacts with the Gβ subunit through two main contacts: sSer1 interactions with βAsp186 and βTyr145 residues, and sLys4 interactions with βMet188 through a Van der Waals interaction and βAsn230, βAsp246 and βAsp228 through hydrogen bonded or charged interactions. In the expression system utilized herein, Asp228Ala and Asp246Ala did not dimerize with gamma and could not

TABLE 10

| | % of Wild-Type Signal | | | | | | |
|---|---|---|---|---|---|---|---|
| | C-Terminal Interface | | | | Shared | | |
| Peptide | Trp332 | Lys57 | Tyr59 | Trp99 | Leu117 | Met101 | Met188 |
| Group I | | | | | | | |
| 3.14 | 7.1 ± 3.7 | 18.6 ± 4.6 | 24.7 ± 15.2 | 66.0 ± 7.7 | 2.1 ± 2.4 | 26.8 ± 12.5 | 2.5 ± 3.7 |
| 2F | −1.5 ± 3.6 | −4.5 ± 6.2 | −2.0 ± 9.5 | 32.6 ± 26.3 | 2.1 ± 5.5 | 6.0 ± 5.1 | 8.5 ± 5.2 |
| C1 | −0.3 ± 2.5 | 0.1 ± 1.6 | 0.3 ± 0.7 | 1.2 ± 2.7 | 5.2 ± 3.1 | 70.5 ± 35.3 | 4.0 ± 3.4 |
| Group II | | | | | | | |
| C14 | 1.6 ± 2.4 | 3.0 ± 5.0 | 3.6 ± 2.0 | 10.1 ± 3.3 | 3.8 ± 9.2 | 1.1 ± 4.9 | 9.9 ± 3.8 |
| 3C | −0.3 ± 1.7 | 3.6 ± 7.5 | 8.5 ± 6.4 | −0.5 ± 5.9 | 10 ± 13.3 | −4.2 ± 5.5 | −5.7 ± 5.6 |
| Group III | | | | | | | |
| C4 | 1.7 ± 3.0 | −0.2 ± 1.9 | 7.6 ± 9.6 | 67.0 ± 15.2 | 18.4 ± 7.1 | 61.2 ± 30.9 | 127.5 ± 22.4 |
| C5 | 3.2 ± 3.7 | 5.6 ± 5.3 | 73.8 ± 16.6 | 39.0 ± 3.8 | 28.5 ± 5.2 | 47.8 ± 18.9 | 97.2 ± 14.2 |
| C8 | 0.7 ± 2.4 | 14.2 ± 9.8 | 4.0 ± 6.2 | −0.8 ± 2.7 | 24.7 ± 12.5 | 23.6 ± 8.5 | 122.6 ± 26.2 |
| Group IV | | | | | | | |
| C2 | 4.7 ± 6.2 | −1.2 ± 4.5 | −1.7 ± 4.8 | −1.0 ± 5.1 | 1.5 ± 5.5 | 157.1 ± 51.5 | −0.7 ± 2.5 |

| | N-Terminal Interface | | | | Indirect | |
|---|---|---|---|---|---|---|
| Peptide | Asn230 | Asp246 | Tyr145 | Asp186 | His311 | Arg314 |
| Group I | | | | | | |
| 3.14 | 22.4 ± 4.2 | 66.5 ± 7.5 | 0.8 ± 0.9 | 14.4 ± 13.4 | 93.4 ± 21.5 | 50.2 ± 5.0 |
| 2F | 27.6 ± 19.1 | 0.6 ± 2.5 | 0.1 ± 6.5 | 2.4 ± 3.5 | 23.6 ± 46.0 | 2.4 ± 3.9 |
| C1 | 19.8 ± 12.3 | 2.3 ± 3.0 | 88.0 ± 29.9 | 1.4 ± 1.7 | 3.0 ± 4.0 | 2.8 ± 1.6 |
| Group II | | | | | | |
| C14 | 60.0 ± 26.5 | 6.3 ± 13.9 | 1.9 ± 5.9 | 3.6 ± 1.9 | 6.1 ± 3.4 | 3.9 ± 7.9 |
| 3C | 4.1 ± 4.4 | 2.0 ± 2.7 | 2.7 ± 10.5 | 35.0 ± 17.2 | 30.5 ± 18.9 | 8.3 ± 3.6 |
| Group III | | | | | | |
| C4 | 11.5 ± 6.0 | 35.8 ± 7.4 | 4.4 ± 3.8 | 51.3 ± 15.0 | 36.5 ± 8.3 | 1.4 ± 1.0 |
| C5 | 33.5 ± 7.2 | 56.3 ± 4.1 | 16.7 ± 4.8 | 45.7 ± 5.2 | 58.7 ± 14.4 | 76.5 ± 6.7 |
| C8 | 74.8 ± 14.8 | 60.8 ± 14.4 | 17.5 ± 7.8 | 124.9 ± 29.1 | 51.6 ± 13.2 | 20.8 ± 11.1 |
| Group IV | | | | | | |
| C2 | 0.0 ± 3.3 | 5.9 ± 5.7 | 4.5 ± 8.1 | 267.2 ± 40.6 | 11.7 ± 8.0 | 1.3 ± 3.1 |

Wild-type or alanine-substituted biotinylated Gβ₁γ₂ subunits were immobilized on a streptavidin-coated 96-well plate, followed by the, addition of phage.
Phage binding was assessed as described herein.
Data was corrected for non-specific binding of phage to the plate and is represented as a percent wild-type-binding.
Data shown are mean ± SD of duplicate determinations from three independent experiments.

Unexpectedly, each of the peptides utilized unique combinations of amino acids within the SIGK binding surface for its particular interaction. A dominant feature amongst the peptides was a strong requirement for Trp332, within the C-terminal interface. Lys57, Tyr59, Leu117, also within this interface, generally contributed significantly to binding the peptides, though there were cases where their effects were not absolutely required. The remainder of the amino acids had more variable effects on binding of each peptide, For example, SIGK has a minimal requirement for Trp99 while be purified; however, Asp246Ser was expressed and purified. In general, peptides in groups I, II and IV have a substantial requirement for binding to the N-terminal region, reflected by an almost complete loss of binding to the Met188Ala and Asp246Ser (except SIGK) mutants and various requirements for Asn230.

Peptides in groups I, II and IV have a conserved motif where a lysine is spaced three amino acids away from a hydrophobic core motif (see Table 9). This motif in SIGK provides the appropriate spacing in a single alpha-helical turn between the lysine that interacts with the N-terminal binding surface and the Ile-Leu-Gly motif that interacts with the C-terminus. It is believed that some of the other peptides adopt a similar α-helical structure that may make this spacing critical. The peptides in group III bind the C-terminal interaction region, but lack a requirement for Met188 and have minimal requirements for Asn230 and Asp246, indicating they do not use the N-terminal binding surface for their interaction with β.

Two amino acids that do not apparently bind directly to SIGK were also analyzed, Arg314 and His311. Replacement of Arg314 results in a modest decrease in SIGK binding; however, for other peptides, Arg314 is absolutely required indicating that they may directly interact with this amino acid. His311 lies well outside the SIGK peptide binding site but was mutated because of its potential involvement in a conformation change in βγ subunits (Gaudet, et al. (1996) supra; Loew, et al. (1998) supra). The imidazole side chain of His311 is 13 Å from the guanido nitrogen of Arg314, the closest amino acid that apparently interacts with any of the peptides. It is unlikely that His311 could directly interact with amino acids from the phage display-derived peptides. Nevertheless, mutation of His311 to alanine affected binding of various peptides to varying extents. Peptides whose binding was affected by His311A also required Arg314 for binding, an effect possibly due to an alteration in the position of Arg314.

It has been demonstrated that two peptides predicted to bind at the Gα-Gβγ interface, βARK-ct peptide (amino acids 643-670) and QEHA, blocked heterotrimer formation but could not promote heterotrimer dissociation (Ghosh, et al. (2003) supra). The crystal structure of the GRK2 (βARK)-Gβγ complex reveals that the surface interacting with the βARK-ct peptide partially overlaps with the SIGK and Gα-switch II binding site (Lambright, et al. (1996) supra; Wall, et al. (1995) supra; Lodowski, et al. (2003) supra). In particular, amino acids Trp99, Trp332, and Try59 within the hydrophobic pocket are common interaction sites in all three structures. The SIGK peptide and a switch II have a lysine residue occupying nearly identical positions on Gβ. Although the βARK-ct peptide has a lysine residue in a similar position, the geometry and nature of the interaction is different. βARK interacts only with Asp228 whereas SIGK and Gα interact with Asp228, Asp246, Asn230 and Met188. Based on this difference, it was determined whether the specific interactions of SIGK at this interface were critical for promoting dissociation.

To examine subunit dissociation, the SCAR peptide, another peptide derived from the phage display screen, was used. Amino acids within the N-terminal interaction interface, Asn230, Asp246 and Met188, contacting sLys4 of SIGK, are not important for binding SCAR. SCAR lacks a lysine residue with the correct positioning relative to the hydrophobic core motif to reach the lysine-binding N-terminal surface (Table 9). Therefore, SCAR would not be able to promote subunit dissociation. Both SIGK and SCAR can compete with Gα$_i$ for binding to Gβ$_3$γ$_2$, with IC$_{50}$'s of 0.5 and 1.7 µM, respectively. However, unlike the SIGK peptide, saturating concentrations of SCAR peptide could not promote dissociation of a preformed heterotrimer. Concentrations of up to 160 µM SCAR, (four times the saturating concentration) did not cause dissociation. The inability of SCAR to promote heterotrimer dissociation was not due to its lower binding affinity since SIRK has a similar affinity and promotes dissociation. These results indicate that peptide binding to the N-terminal interface is necessary for acceleration of heterotrimer dissociation.

To more directly assess the importance of peptide binding to the N-terminal peptide binding interface, the sLys4 residue of SIRK was mutated to alanine, eliminating the key contact to the N-terminal binding pocket. This peptide had a markedly lower affinity than SIRK (IC$_{50}$=60 µM vs 1.4 µM) for blocking Gα-Gβγ interactions; however, at high concentrations, it blocked to levels near that of SIRK. Despite blocking Gα-Gβγ interactions, SIRK(Lys4Ala) failed to accelerate heterotrimer dissociation. The apparent off-rate of Fα$_{i1}$ appears slower for SIRK(Lys4Ala) relative to the intrinsic dissociation rate. This could be because SIRK(Lys4Ala) is low affinity blocker, and is not effective at preventing rebinding of Fα$_{i1}$. To confirm that the low affinity of SIRK(Lys4Ala) was not responsible for the inability to accelerate dissociation, a peptide with comparable affinity to SIRK(Lys4Ala), SIRK(Gly10Ala) (IC$_{50}$~80 µM), was tested. This peptide has Lys4 but Ala is substituted for Gly at position 10, thus SIRK (Gly10Ala) retains binding to the N-terminal interface but has a reduced affinity due to decreased interactions with the C-terminal region. SIRK(Gly10Ala) blocked heterotrimer formation at high peptide concentrations and despite having a low affinity for Gβγ, could still accelerate heterotrimer dissociation.

SIGK binds to Gβ$_1$ at a region occupied by the switch II domain of Gα subunits in the heterotrimer. The crystal structure of the heterotrimer reveals the switch interface (composed of switch I and switch II) of Gα buries approximately 1,800 Å of Gβ through numerous contacts (Lambright, et al. (1996) supra, Wall, et al. (1995) supra); however, the effects of mutations of β subunit amino acids at this interface on α subunit binding have not been measured in direct binding assays near the K$_d$ for Gα-Gβγ interactions. Switch I and switch II undergo large conformational changes upon GTP binding and it is thought these changes mediate heterotrimer dissociation.

Gβ$_1$ subunit mutants disclosed herein were isolated from insect cells as a complex with Gγ$_2$ and hexa-histidine-tagged Gα$_{i1}$ indicating that many of these contacts between the subunits predicted from the crystal structures were not individually critical for Gα subunit binding. To determine which amino acids were contributing to the ability of peptides to enhance dissociation rate constants, the dissociation rate constant (k$_{off}$) for Fα$_{i1}$ from each of the individually substituted b-β$_1$γ$_2$ mutants was measured. The intrinsic off-rate for wild-type was 0.123 s-1, corresponding well with previous measurements (Sarvazyan, et al. (1998) *J. Biol. Chem.* 273:7934-7940). Data from all of these mutants are shown in Table 11.

TABLE 11

| Mutation | K$_{off}$** |
|---|---|
| Wild-Type | 0.123 ± 0.0429 min$^{-1}$ |
| Lys57Ala | 0.144 ± 0.0441 min$^{-1}$ |
| Tyr59Ala | 0.181 ± 0.0726 min$^{-1}$ |
| Trp99Ala | 0.288 ± 0.0547 min$^{-1}$ |
| Met101Ala | 0.114 ± 0.0175 min$^{-1}$ |
| Leu117Ala | 0.361 ± 0.0258 min$^{-1}$ |
| Tyr145Ala | 0.155 ± 0.0423 min$^{-1}$ |
| Asp186Ala | 0.160 ± 0.0429 min$^{-1}$ |
| Met188Ala | 0.122 ± 0.0380 min$^{-1}$ |
| Asn230Ala | 0.148 ± 0.0488 min$^{-1}$ |
| Asp246Ser† | — |
| Arg314Ala | 0.118 ± 0.0246 min$^{-1}$ |
| Trp332Ala | 0.301 ± 0.0420 min$^{-1}$ |

**Mean ± SD from four independent experiments.
Statistically significant as compared to wild-type (p < 0.05) as determined by a one-way ANOVA followed by independent linear contrasts.
†k$_{off}$ could not be measured because significant stable binding of F-α$_i$ was not detectable.

The results showed that of the 12 mutants tested, Trp99Ala, Leu117Ala, and Trp332Ala were statistically different from wild-type with relatively minor increases in $k_{off}$. On the other hand, Asp246Ser, despite being able to be purified based on 6HisGα$_i$ binding (although in low yield from a large culture), was unable to stably bind F-α$_{i1}$ in the flow cytometry assay at the low concentrations used for this assay. This indicates that interactions with Asp246 are critical for stable Gα subunit interactions, while individual interactions in the primarily hydrophobic C-terminal interface are not as important.

Example 9

Small Molecule Library Screen

A phage ELISA assay was used to determine whether small molecules identified in the computational screen could interact with the Gβγ protein interaction surface. Phage displaying the SIGK peptide were used in accordance with established methods (Scott, et al. (2001) supra; Smrcka and Scott (2002) supra). The screen was based on a reduction in the optical density (OD) of wells containing Gβγ subunits and phage. In each plate, three wells contained positive controls for binding that included b-βγ subunits, SIGK-phage, and the appropriate amount of vehicle. Three background wells contained no βγ subunits.

As disclosed herein, biotinylated Gβγ subunits were immobilized on the surface of a 96-well plate coated with streptavidin, phage displaying Gβγ-binding peptides were subsequently added and binding in the presence and absence of test compounds detected with an anti-phage antibody.

Example 10

Inhibition of Gβγ Signaling in Neutrophils $Ca^{2+}$ fluxes were measured using two 35 mL cultures of differentiated HL-60 neutrophil cultures ($0.2 \times 10^6$ cells/mL). Cells were cultured for three days with in DMSO (1.2%), washed in HSS and resuspended in 2 mL HBSS at a concentration of $7 \times 10^6$ cells/mL. Addition of DMSO to the growth medium induces differentiation of these cells into morphologically and functionally mature neutrophils (Collins, et al. (1978) *Proc. Natl. Acad. Sci. USA* 75:2458; Collins, et al., (1979) *J. Exp. Med.* 149:969). Neutrophils were preloaded with fura-2 (1 µM), a fluorescent $Ca^{2+}$-sensitive indicator (Suh, et al., (1996) *J. Biol. Chem.* 271:32753), for 45 minutes, washed with HBSS and resuspended in 2 mL of indicator-free HBSS. An 140 µL aliquote of cells was added to a total of 2 mL HBSS. Fluorescence ratios were taken by dual excitation at 340 and 380 nm and emission at 510 nm. After a stable baseline was established, either DMSO or NSC119910 was added and incubated for 5 minutes. Subsequently, either fMLP or ATP agonists were added to activate release of $Ca^{2+}$ from intracellular stores.

---

What is claimed is:

1. A method for ameliorating or treating a disease or condition in a subject in need thereof, wherein the disease or condition involves at least one G protein βγ subunit activity, the method comprising administering to the subject a therapeutically effective amount of a therapeutically acceptable composition comprising a compound that binds to at least one amino acid residue of the protein interaction site of the G protein β subunit,
   wherein the protein binding site comprises at least one amino acid selected from the group consisting of Lys57, Tyr59, Trp99, Val100, Met101, Leu117, Tyr145, Asp186, Met188, Asp228, Asn230, Asp246, and Trp332 of SEQ ID NO:3 or 4,
   wherein the compound is a compound of Formula III or a salt thereof:

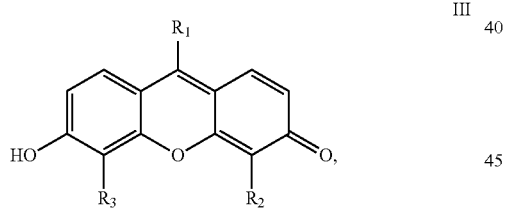

wherein:
   $R_1$ is substituted or unsubstituted alkyl, substituted or unsubstituted alkenyl, substituted or unsubstituted cycloalkyl, or substituted or unsubstituted cycloalkenyl; and
   $R_2$ and $R_3$ are independently —H or —OH;
wherein the disease or condition is opioid tolerance; whereby the disease or condition in the subject is ameliorated or treated in the subject.

2. The method of claim 1, wherein $R_2$ and $R_3$ are —OH.

3. The method of claim 1, wherein the substituents in the substituted alkyl, cycloalkyl, alkenyl or cycloalkenyl groups independently comprise hydroxy, carboxy, halogen, substituted alkyl, or unsubstituted alkyl.

4. The method of claim 1, wherein $R_1$ is carboxy-substituted alkyl, carboxy-substituted cycloalkyl, carboxy-substituted alkenyl, or carboxy-substituted cycloalkenyl.

5. The method of claim 1, wherein the compound is selected from the group consisting of:

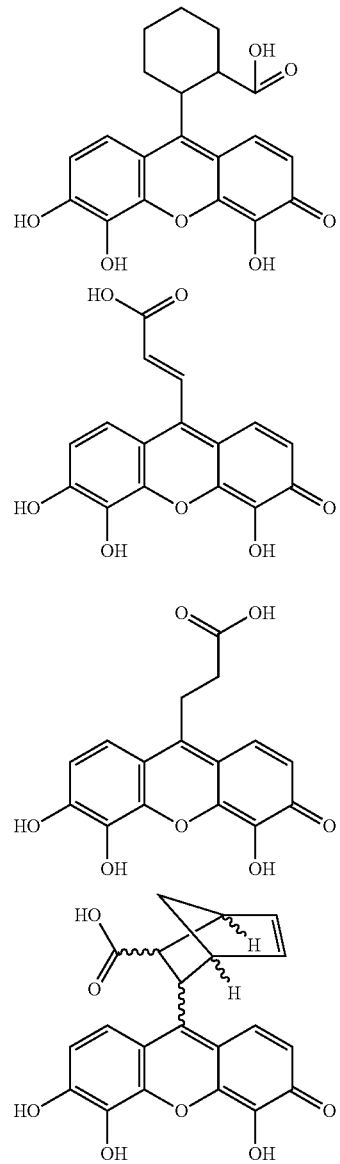

-continued
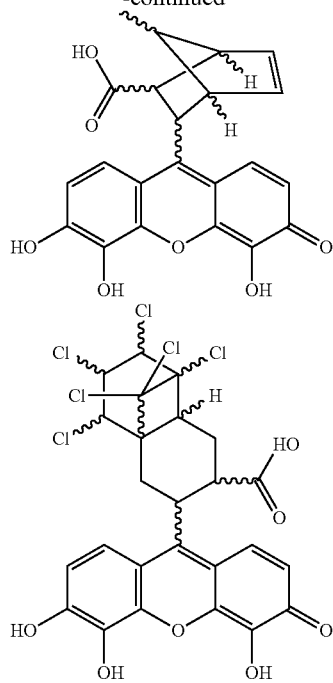
-continued
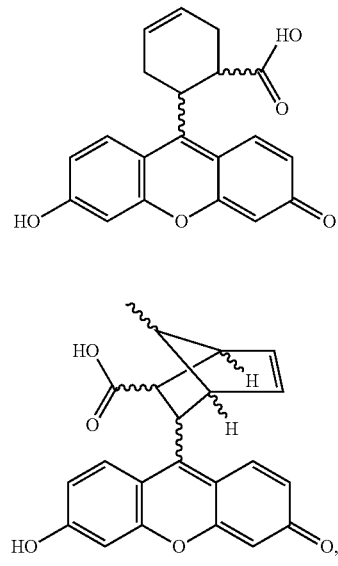
any salts thereof, and any combinations thereof.
* * * * *

SEQUENCE LISTING

<160> NUMBER OF SEQ ID NOS: 13

<210> SEQ ID NO 1
<211> LENGTH: 15
<212> TYPE: PRT
<213> ORGANISM: Artificial Sequence
<220> FEATURE:
<223> OTHER INFORMATION: Synthetic peptide

<400> SEQUENCE: 1

Ser Ile Arg Lys Ala Leu Asn Ile Leu Gly Tyr Pro Asp Tyr Asp
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: Synthetic peptide

<400> SEQUENCE: 2

Ser Ile Gly Lys Ala Phe Lys Ile Leu Gly Tyr Pro Asp Tyr Asp
1               5                   10                  15

<210> SEQ ID NO 3
<211> LENGTH: 340
<212> TYPE: PRT
<213> ORGANISM: Rattus norvegicus

<400> SEQUENCE: 3

Met Gly Glu Met Glu Gln Leu Lys Gln Glu Ala Glu Gln Leu Lys Lys
1               5                   10                  15

Gln Ile Ala Asp Ala Arg Lys Ala Cys Ala Asp Ile Thr Leu Ala Glu
            20                  25                  30

Leu Val Ser Gly Leu Glu Val Val Gly Arg Val Gln Met Arg Thr Arg

```
            35                  40                  45
Arg Thr Leu Arg Gly His Leu Ala Lys Ile Tyr Ala Met His Trp Ala
 50                  55                  60

Thr Asp Ser Lys Leu Leu Val Ser Ala Ser Gln Asp Gly Lys Leu Ile
 65                  70                  75                  80

Val Trp Asp Thr Tyr Thr Thr Asn Lys Val His Ala Ile Pro Leu Arg
                     85                  90                  95

Ser Ser Trp Val Met Thr Cys Ala Tyr Ala Pro Ser Gly Asn Phe Val
                100                 105                 110

Ala Cys Gly Gly Leu Asp Asn Met Cys Ser Ile Tyr Ser Leu Lys Ser
                115                 120                 125

Arg Glu Gly Asn Val Lys Val Ser Arg Glu Leu Ser Ala His Thr Gly
130                 135                 140

Tyr Leu Ser Cys Cys Arg Phe Leu Asp Asp Asn Asn Ile Val Thr Ser
145                 150                 155                 160

Ser Gly Asp Thr Thr Cys Ala Leu Trp Asp Ile Glu Thr Gly Gln Gln
                165                 170                 175

Lys Thr Val Phe Val Gly His Thr Gly Asp Cys Met Ser Leu Ala Val
                180                 185                 190

Ser Pro Asp Tyr Lys Leu Phe Ile Ser Gly Ala Cys Asp Ala Ser Ala
                195                 200                 205

Lys Leu Trp Asp Val Arg Glu Gly Thr Cys Arg Gln Thr Phe Thr Gly
                210                 215                 220

His Glu Ser Asp Ile Asn Ala Ile Cys Phe Phe Pro Asn Gly Glu Ala
225                 230                 235                 240

Ile Cys Thr Gly Ser Asp Asp Ala Ser Cys Arg Leu Phe Asp Leu Arg
                245                 250                 255

Ala Asp Gln Glu Leu Thr Ala Tyr Ser His Glu Ser Ile Ile Cys Gly
                260                 265                 270

Ile Thr Ser Val Ala Phe Ser Leu Ser Gly Arg Leu Leu Phe Ala Gly
                275                 280                 285

Tyr Asp Asp Phe Asn Cys Asn Val Trp Asp Ser Leu Lys Cys Glu Arg
                290                 295                 300

Val Gly Val Leu Ser Gly His Asp Asn Arg Val Ser Cys Leu Gly Val
305                 310                 315                 320

Thr Ala Asp Gly Met Ala Val Ala Thr Gly Ser Trp Asp Ser Phe Leu
                325                 330                 335

Lys Ile Trp Asn
                340

<210> SEQ ID NO 4
<211> LENGTH: 340
<212> TYPE: PRT
<213> ORGANISM: Homo sapiens
<220> FEATURE:
<221> NAME/KEY: misc_feature
<222> LOCATION: 107
<223> OTHER INFORMATION: xaa can be any naturally occurring amino acid

<400> SEQUENCE: 4

Met Ser Glu Leu Glu Gln Leu Arg Gln Glu Ala Glu Gln Leu Arg Asn
 1               5                  10                  15

Gln Ile Arg Asp Ala Arg Lys Ala Cys Gly Asp Ser Thr Leu Thr Gln
                20                  25                  30

Ile Thr Ala Gly Leu Asp Pro Val Gly Arg Ile Gln Met Arg Thr Arg
                35                  40                  45
```

```
Arg Thr Leu Arg Gly His Leu Ala Lys Ile Tyr Ala Met His Trp Gly
 50                  55                  60

Thr Asp Ser Arg Leu Leu Val Ser Ala Ser Gln Asp Gly Lys Leu Ile
 65                  70                  75                  80

Ile Trp Asp Ser Tyr Thr Thr Asn Lys Val His Ala Ile Pro Leu Arg
                 85                  90                  95

Ser Ser Trp Val Met Thr Cys Ala Tyr Ala Xaa Ser Gly Asn Phe Val
            100                 105                 110

Ala Cys Gly Gly Leu Asp Asn Ile Cys Ser Ile Tyr Ser Leu Lys Thr
        115                 120                 125

Arg Glu Gly Asn Val Arg Val Ser Arg Glu Leu Pro Gly His Thr Gly
    130                 135                 140

Tyr Leu Ser Cys Cys Arg Phe Leu Asp Asp Asn Gln Ile Ile Thr Ser
145                 150                 155                 160

Ser Gly Asp Thr Thr Cys Ala Leu Trp Asp Ile Glu Thr Gly Gln Gln
                165                 170                 175

Thr Val Gly Phe Ala Gly His Ser Gly Asp Val Met Ser Leu Ser Leu
            180                 185                 190

Ala Pro Asn Gly Arg Thr Phe Val Ser Gly Ala Cys Asp Ala Ser Ile
        195                 200                 205

Lys Leu Trp Asp Val Arg Asp Ser Met Cys Arg Gln Thr Phe Ile Gly
    210                 215                 220

His Glu Ser Asp Ile Asn Ala Val Ala Phe Phe Pro Asn Gly Tyr Ala
225                 230                 235                 240

Phe Thr Thr Gly Ser Asp Asp Ala Thr Cys Arg Leu Phe Asp Leu Arg
                245                 250                 255

Ala Asp Gln Glu Leu Leu Met Tyr Ser His Asp Asn Ile Ile Cys Gly
            260                 265                 270

Ile Thr Ser Val Ala Phe Ser Arg Ser Gly Arg Leu Leu Leu Ala Gly
        275                 280                 285

Tyr Asp Asp Phe Asn Cys Asn Ile Trp Asp Ala Met Lys Gly Asp Arg
    290                 295                 300

Ala Gly Val Leu Ala Gly His Asp Asn Arg Val Ser Cys Leu Gly Val
305                 310                 315                 320

Thr Asp Asp Gly Met Ala Val Ala Thr Gly Ser Trp Asp Ser Phe Leu
                325                 330                 335

Lys Ile Trp Asn
            340

<210> SEQ ID NO 5
<211> LENGTH: 15
<212> TYPE: PRT
<213> ORGANISM: Artificial Sequence
<220> FEATURE:
<223> OTHER INFORMATION: Synthetic peptide

<400> SEQUENCE: 5

Ser Ile Gly Lys Ala Leu Phe Ile Leu Gly Tyr Pro Asp Tyr Asp
 1               5                  10                  15

<210> SEQ ID NO 6
<211> LENGTH: 13
<212> TYPE: PRT
<213> ORGANISM: Artificial Sequence
<220> FEATURE:
<223> OTHER INFORMATION: Synthetic peptide

<400> SEQUENCE: 6
```

```
Leu Cys Ser Lys Ala Tyr Leu Leu Gly Gln Thr Cys
1               5                   10
```

<210> SEQ ID NO 7
<211> LENGTH: 15
<212> TYPE: PRT
<213> ORGANISM: Artificial Sequence
<220> FEATURE:
<223> OTHER INFORMATION: Synthetic peptide

<400> SEQUENCE: 7

```
Ser Cys Lys Arg Thr Lys Ala Gln Ile Leu Leu Ala Pro Cys Thr
1               5                   10                  15
```

<210> SEQ ID NO 8
<211> LENGTH: 15
<212> TYPE: PRT
<213> ORGANISM: Artificial Sequence
<220> FEATURE:
<223> OTHER INFORMATION: Synthetic peptide

<400> SEQUENCE: 8

```
Trp Cys Pro Pro Lys Ala Met Thr Gln Leu Gly Ile Lys Ala Cys
1               5                   10                  15
```

<210> SEQ ID NO 9
<211> LENGTH: 16
<212> TYPE: PRT
<213> ORGANISM: Artificial Sequence
<220> FEATURE:
<223> OTHER INFORMATION: Synthetic peptide

<400> SEQUENCE: 9

```
Ser Cys Gly His Gly Leu Lys Val Gln Ser Thr Ile Gly Ala Cys Ala
1               5                   10                  15
```

<210> SEQ ID NO 10
<211> LENGTH: 12
<212> TYPE: PRT
<213> ORGANISM: Artificial Sequence
<220> FEATURE:
<223> OTHER INFORMATION: Synthetic peptide

<400> SEQUENCE: 10

```
Ser Cys Glu Lys Arg Tyr Gly Ile Glu Phe Cys Thr
1               5                   10
```

<210> SEQ ID NO 11
<211> LENGTH: 12
<212> TYPE: PRT
<213> ORGANISM: Artificial Sequence
<220> FEATURE:
<223> OTHER INFORMATION: Synthetic peptide

<400> SEQUENCE: 11

```
Ser Cys Glu Lys Arg Leu Gly Val Arg Ser Cys Thr
1               5                   10
```

<210> SEQ ID NO 12
<211> LENGTH: 12
<212> TYPE: PRT
<213> ORGANISM: Artificial Sequence

```
<220> FEATURE:
<223> OTHER INFORMATION: Synthetic peptide

<400> SEQUENCE: 12

Ser Cys Ala Arg Phe Phe Gly Thr Pro Gly Cys Thr
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic peptide

<400> SEQUENCE: 13

Trp Cys Pro Pro Lys Leu Glu Gln Trp Tyr Asp Gly Cys Ala
1               5                   10
```